(12) United States Patent
Gayral et al.

(10) Patent No.: US 7,718,402 B2
(45) Date of Patent: May 18, 2010

(54) BIOLOGICAL REAGENTS AND METHODS TO VERIFY THE EFFICIENCY OF SAMPLE PREPARATION AND NUCLEIC ACID AMPLIFICATION AND/OR DETECTION

(75) Inventors: Jean Pierre Gayral, Sainte-Foy (CA); Francois Picard, Cap-Rouge (CA); Maurice Boissinot, Saint-Augustin-de-Desmaures (CA); Martine Bastien, Beauport (CA)

(73) Assignee: Geneohm Sciences Canada Inc., Quebec (CA)

( * ) Notice: Subject to any disclaimer, the term of this patent is extended or adjusted under 35 U.S.C. 154(b) by 0 days.

(21) Appl. No.: 10/538,442

(22) PCT Filed: Dec. 15, 2003

(86) PCT No.: PCT/CA03/01925

§ 371 (c)(1),
(2), (4) Date: Sep. 11, 2006

(87) PCT Pub. No.: WO2004/055205

PCT Pub. Date: Jul. 1, 2004

(65) Prior Publication Data

US 2007/0015139 A1    Jan. 18, 2007

(51) Int. Cl.
C12P 19/34    (2006.01)
(52) U.S. Cl. ..................................................... 435/91.2
(58) Field of Classification Search .................. 435/91.2
See application file for complete search history.

(56) References Cited

U.S. PATENT DOCUMENTS

| 4,683,195 | A | 7/1987 | Mullis et al. |
| 4,683,202 | A | 7/1987 | Mullis |
| 4,800,159 | A | 1/1989 | Mullis et al. |
| 4,965,188 | A | 10/1990 | Mullis et al. |
| 5,994,078 | A | 11/1999 | Rundell et al. |
| 6,074,825 | A | 6/2000 | Rundell et al. |

FOREIGN PATENT DOCUMENTS

| WO | WO 99/006594 | | 2/1999 |
| WO | WO 02/018635 | | 3/2002 |
| WO | WO 0218635 | * | 3/2002 |
| WO | WO 03/008636 | | 1/2003 |
| WO | WO 2004/055205 | | 7/2004 |

OTHER PUBLICATIONS

Ke et al. Clinical Chemisty, vol. 46, No. 3, pp. 324-331, 2000.*
Saldanha, John. Journal of Clinical Virology, vol. 20, pp. 7-13, Jan. 2001.*
Picard and Bergeron, Drug Discovery Today, vol. 7, issue 2, pp. 1092-1101, Nov. 2002.*
Kuske et al. Applied and Environmental Microbiology, vol. 64, No. 7, pp. 2463-2472, Jul. 1998.*
Kolk et al. Journal of Clinical Microbiology, vol. 32, No. 5, pp. 1354-1356, May 1994.*
Ausubel et al., Current Protocols in Molecular Biology (1987-2004) [Table of Contents Only].
Bélanger et al., "Rapid detection of Shiga toxin-producing bacteria in feces by multiplex PCR with molecular beacons on the smart cycler", *Journal of Clinical Microbiology* (2002) 40(4):1437.
Bergeron et al., "Rapid detection of group B streptococci in pregnant women at delivery", *New Engl. J. Med.* (2000) 343(3):175-179.
Brightwell et al., "Development of internal controls for PCR detection of *Bacillus anthracis*", *Mol. Cell Probes* (1998) 12(6):367-377.
Courtney et al., "Development of internal controls for probe-based nucleic acid diagnostic assays," *Anal. Biochem.* (1999) 270(2):249-256.
Ehrlich et al., PCR-based Diagnostics in Infectious Diseases (1994). [Table of Contents only].
Innis et al., PCR protocols: A Guide to Method And Applications (1990). [Table of Contents only].
International Search Report for International Patent Application No. PCT/CA2003/001925 dated Jun. 23, 2004.
Kwoh et al., "Target amplication systems in nucleic acid-based diagnostic approaches", *Am. Biotechnol. Lab.* (1990) 8(13):14-25.
Kwoh et al., "Transcription-based amplification system and detection of amplified human immunodeficiency virus type 1 with a bead-based sandwich hybridization format", *Proc. Natl. Acad. Sci. USA* (1989) 1173-1177.
Leblanc et al., "Less than one hour detection of *Bacillus anthracis* spores and vegetative cells from clinical specimens by fluorescence-based PCR", In *102nd General Meeting of the American Society for Microbiology* (2002) abstract No. C-257.
Lizardi et al., "Exponential amplification of recombinant-RNA Hybridization Probes", *Bio/Technology* (1988) 6:1197-1202.
Malek et al., "Nucleic acid sequence-based amplification (NASBA)", *Methods Mol. Biol.* (1994) 28:253-260.
Morré et al., "RNA amplification by nucleic acid sequence-based amplification with an internal standard enables reliable detection of *Chlamydia trachomatis* in cervical scrapings and urine samples", *J. Clin. Microbiol* (1996) 34(12):3108-3114.

(Continued)

*Primary Examiner*—Gary Benzion
*Assistant Examiner*—Cynthia B Wilder
(74) *Attorney, Agent, or Firm*—Knobbe Martens Olson & Bear LLP

(57) ABSTRACT

This invention relates to reagent comprising: any one of cells, viral particles, organelles, parasites, cells comprising organelles, cells comprising viral particles, cells comprising parasites, cells comprising bacterial cells and any combination thereof, the cells, viral particles, organelles or parasites comprising at least one nucleic acid sequence serving as an internal control (IC) target for nucleic acid testing (NAT) assay; wherein the reagent is suitable to be added to a test sample undergoing sample preparation to release, concentrate and/or purify nucleic acids and amplification and/or detection of nucleic acids so as to be used to verify: (i) the efficiency of sample preparation; and (ii) the efficiency of nucleic acid amplification and/or detection. The present invention also relates to a method to verify or validate the preparation and amplification and/or detection of a nucleic acid target sequence in a sample spiked with a reagent of the present invention.

37 Claims, 8 Drawing Sheets

OTHER PUBLICATIONS

Morse et al., Nucleic Acid Amplification Technologies: Application to Disease Diagnosis (1997). [Table of Contents only].

Murray et al, Manual of Clinical Microbiology 8$^{th}$ Ed (2003). [Table of Contents only].

Nolte et al., "Molecular detection and identification of microorganisms", in Murray et al., *Manual of clinical microbiology, 8$^{th}$ ed.* (2003):234-256.

Persing et al., Diagnostic Molecular Microbiology: Principles and Applications (1993). [Table of Contents only].

Rosenstraus et al., "An internal control for routine diagnostic PCR: design, properties, and effect on clinical performance", *J. Clin. Microbiol.* (1998) 36(1):191-197.

Sachadyn et al., "The construction and use of a PCR internal control", *Mol. Cell. Probes* (1998) 12(5):259-262.

Sambrook et al., Molecular Cloning: A Laboratory Manual (1989). [Table of Contents only].

Sambrook et al., Molecular Cloning: A Laboratory Manual (2001). [Table of Contents only].

Stöcher et al., "A convenient approach to the generation of multiple internal control DNA for a panel of real-time PCR assays", *J. Virol. Methods* (2002), 108:1-8.

Trépanier et al., "One-hour detection of *Candida albicans* and *Candida dubliniensis* in blood samples using the Smart Cycler (R)", in *101$^{st}$ General Meeting, ASM,* Orlando, Fl (2001) 1-3. Abstract.

URSI et al., "Construction of an internal control for the detection of *Chlamydia pneumoniae* by PCR", *Molecular Cellular Probes* (1998) 12(4):235-238.

Walker et al., "Strand displacement amplification-an isothermal, in vitro DNA amplification technique", *Nucleic Acids Res.* (1992) 20(7):1691-1696.

Weiss, "Hot prospect for new gene amplifier" *Science* (1991) 254(5036):1292-1293.

* cited by examiner

SEQUENCE LISTING

<160> NUMBER OF SEQ ID NOS: 11

<210> SEQ ID NO 1
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 1
tttcaccagc tgtattagaa gta                                        23

<210> SEQ ID NO 2
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 2
gttccctgaa cattatcttt gat                                        23

<210> SEQ ID NO 3
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 3
ccacgcccca gcaaatggct caaaagcgcg tgg                             33

<210> SEQ ID NO 4
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 4
ccacgcgaaa ggtggagcaa tgtgaaggcg tgg                             33

<210> SEQ ID NO 5
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 5
ggatcaaacg gcctgcaca                                             19

<210> SEQ ID NO 6
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 6
caaatattat ctcgtaattt accttgttc                                  29

-continued

```
<210> SEQ ID NO 7
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 7
cacttcattt aggcgacgat act                                           23

<210> SEQ ID NO 8
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 8
ttgtctgtga atcggatctt tctc                                          24

<210> SEQ ID NO 9
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 9
cgtcttacaa cgcagtaact acgcactatc attcagc                            37

<210> SEQ ID NO 10
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 10
cgtcccaatg ttacattacc aaccggcact gaaatagg                           38

<210> SEQ ID NO 11
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 11
atgcctcttc acattgctcc acctttcctg tg                                 32
```

BIOLOGICAL REAGENTS AND METHODS TO VERIFY THE EFFICIENCY OF SAMPLE PREPARATION AND NUCLEIC ACID AMPLIFICATION AND/OR DETECTION

The Sequence Listing in electronic format is provided as a file entitled GENOM.061NP.TXT, created on Oct. 22, 2009, which is 2.48KB in size. The information in the electronic format of the Sequence Listing is incorporated herein by reference in its entirety.

FIELD OF THE INVENTION

The present invention relates to reagents and methods to validate the results obtained in a nucleic acid testing assay. More particularly, the present invention relates to biological reagents and methods to verify the efficiency of sample preparation and nucleic acid amplification and/or detection.

BACKGROUND OF THE INVENTION

With the advent of molecular biology, nucleic acid testing (NAT) assays are becoming increasingly popular. These assays rely on the hybridization of synthetic oligonucleotide primers and/or probes targeting a nucleotide sequence of the organism(s) of interest. Highly sensitive NAT technologies, such as the widely used polymerase chain reaction (PCR), represent important tools in the field of molecular diagnostics. Since the discovery of PCR in 1983, numerous DNA-based assays targeting a wide variety of microbial pathogens have been developed (Nolte and Caliendo, 2003, Molecular detection and identification of microorganisms, p. 234-256, In Manual of Clinical Microbiology ($8^{th}$ ed.), Murray et al., American Society for Microbiology, Washington, D.C.; Lee et al. 1997, Nucleic Acid Amplification Technologies: Application to Disease Diagnosis, Biotechniques Books, Eaton Publishing, Boston, Mass.; Persing et al., 1993, Diagnostic Molecular Microbiology: Principles and Applications, American Society for Microbiology, Washington, D.C.; Ehrlich; Greenberg, 1994, PCR-based Diagnostics in Infectious Disease, Blackwell Scientific Publications, Boston, Mass.). Many of these NAT assays have been designed for microbial detection directly from clinical, environmental or food samples, which are known to contain inhibitors of NAT assays. Over the years, a variety of procedures performed from a variety of test samples for concentration and/or purification of cells or viral particles as well as for release, concentration and/or purification of nucleic acids have been developed. However, samples prepared by these procedures may still contain impurities that interfere with NAT assays.

Numerous studies have demonstrated that many types of clinical, environmental and food specimens may contain substances interfering with nucleic acid amplification processes including PCR, ligase chain reaction (LCR), transcription-mediated amplification (TMA) and strand displacement amplification (SDA) (Courtney et al. 1999, Analytical Biochem. 270:249-256; Rosenstraus et. al., 1998, J. Clin. Microbiol. 36: 191-197; Morré et al. 1996, J. Clin. Microbiol. 34:3108-3114; Lee et al. 1997, Nucleic Acid Amplification Technologies: Application to Disease Diagnosis, Biotechniques, Books, Eaton Publishing, Boston, Mass.; Persing et al., 1993, Diagnostic Molecular Microbiology: Principles and Applications, American Society for Microbiology, Washington, D.C.; Ehrlich and Greenberg, 1994, PCR-based Diagnostics in Infectious Disease, Blackwell Scientific Publications, Boston, Mass.). Therefore, it is crucial to identify inhibitory test samples because negative test results may be attributable to inhibition of the NAT assay by impurities not eliminated, neutralized or inactivated by the protocol used for sample preparation. Inhibitory test samples can be identified by verifying the efficiency of amplification and/or detection of a nucleic acid target serving as a control. Such control may be external when the control nucleic acid is added to a portion of the sample tested in parallel for amplification and/or detection of the control target sequences while another portion of the sample is analyzed for amplification and/or detection of the analyte target sequences to be detected by the assay. Such control is called an "internal control (IC)" when both control target sequences and analyte target sequences are purified and/or detected in the same reaction vessel. More specifically, this internal control system provides an IC for amplification and/or detection (ICAD) of nucleic acids. Inhibitory samples lead to lower or no ICAD signal while a positive signal for the ICAD of the expected intensity demonstrates the absence of nucleic acid amplification/detection inhibitors in the test sample, thereby validating a negative result for the primary target(s). ICAD have been developed by using various strategies (Courtney et al., 1999, Analytical Biochem., 270:249-256; Rosenstraus et al. 1998, J. Clin. Microbiol., 36:191-197; Morré et al., 1996, J. Clin. Microbiol., 34:3108-3114; Stocher et al., 2002, J. Virol. Methods 108:1-8). The IC target nucleic acids may be cloned in diverse cloning vectors including plasmids, cosmids, bacteriophages and transposons (Sambrook and Russel, 2001, Molecular Cloning: A laboratory manual, Cold Spring Harbor Laboratory Press, Cold Spring Harbor, N.Y.).

It is also important to validate the sample preparation method for NAT assays to ensure its efficiency to lyse microbial cells because many microbial species have a thick and/or sturdy cell wall (e.g. gram-positive bacteria, mycobacteria, bacterial spores and yeasts), which make them difficult to lyse. Efficient cell lysis is required to release target nucleic acids to allow their amplification and/or detection. Furthermore, the current trend in molecular diagnostics is to integrate sample preparation and nucleic acid amplification and/or detection into a single device. Therefore, there is a need to develop strategies to validate both the sample preparation procedure and the amplification and/or detection processes.

The inventors have previously demonstrated that popular commercially available kits for rapid microbial DNA isolation were not efficient for nucleic acid recovery from gram-positive bacteria and yeast cells (PCT patent publication WO 03/008636). U.S. Pat. Nos. 5,994,078 and 6,074,825 describe a method to prepare stable encapsulated reference nucleic acids used to monitor genetic testing by providing an external control reaction to verify the efficiency of sample preparation for NAT assays. However, obtaining such sample preparation control vehicles requires chemical and/or physical treatment of the cellular vehicle used to mimic the membrane stability of the test cells. Consequently, the modified cellular vehicle is different from the naturally encountered microbial cells targeted by NAT assays. Moreover, such external controls do not allow a monitoring of the efficiency of amplification and/or detection procedures.

There thus remains a need to provide a means to verify the efficiency of a sample preparation procedure and of the performance of nucleic acid amplification and/or detection. There also remains a need to provide biological reagents to enable such methods. In addition there remains a need to provide methods and reagents, which more truly validate the results obtained with a NAT assay.

The present invention seeks to meet these and other means.

SUMMARY OF THE INVENTION

The present invention describes reagents and methods using cells, and/or viral particles, and/or organelles and/or parasites containing nucleic acid sequences serving as targets for an (IC), to verify the efficiency of a sample preparation method, as well as the performance of nucleic acid amplification and/or detection. These reagents and methods provide an IC for sample preparation and amplification and/or detection (ICSPAD) of nucleic acids. The efficiency of (1) nucleic acid recovery from intact cells, and/or viral particles, and/or organelles, and/or parasites added to each test sample and/or (2) the level of nucleic acid amplification and/or detection inhibition (if present), can be estimated by comparison with external control reaction(s) if required.

The present invention therefore aims at providing a method using cells, viral particles, organelles, parasites or cells comprising organelles, and/or viral particles, and/or another infectious agent (such as a bacteria or parasite) containing nucleic acid sequences serving as a target to verify the efficiency of a sample preparation procedure as well as the performance of nucleic acid amplification and/or detection (i.e. ICSPAD) of the target, the method comprising:

1) providing cells, viral particles, organelles, parasites or cells comprising organelles, and/or viral particles, and/or another infectious agent, carrying a nucleic acid sequence serving as an internal control (IC) target for a nucleic acid-based assay to be performed on a test sample;
2) adding the cells, viral particles and/or organelles to the test sample;
3) subjecting the sample with added cells, viral particles and/or organelles to a sample preparation procedure in order to release nucleic acids therefrom; and
4) subjecting the prepared sample to nucleic acid amplification and/or detection under appropriate conditions.

In another embodiment, following the release of the nucleic acid, it is concentrated and/or purified.

Optionally, the sample preparation method and amplification and/or detection processes are evaluated by comparison to control reaction(s). In one such embodiment external controls are used.

The sample preparation procedure can include (i) concentration and/or purification of cells, viral particles and/or organelles, (ii) lysis of cells, viral particle lysis and/or organelles, (iii) nucleic acid extraction, (iv) elimination, neutralization and/or inactivation of NAT inhibitors, and/or (v) nucleic acid concentration and/or purification. In one embodiment the sample preparation will be limited to a liberation of the targeted nucleic acid which enables as the amplification of same. Minimally, this release or liberation of the nucleic acid can be effected in the first cycles of ampflication (e.g. in the high temperature cycles of the PCR). In another embodiment, the preparation of the sample is more elaborate and comprises one or more of the steps i)-v) listed above. In one particular embodiment, the sample preparation includes steps i)-v)

In a particular embodiment, the cell is a bacteria, a yeast, an organelle or an eukaryotic cell. In another embodiment, the cell is a bacterial endospore (also designated as a "spore"). Microbial cell lysis represents a crucial step in the sample preparation protocol which affects the efficiency of the release of the nucleic acid content of the treated cells. Bacterial spores are generally the cells which are the most difficult to lyse and can therefore serve as a universal control for cell lysis. Moreover, spores are naturally resistant to harsh conditions thereby potentially providing a more stable reagent and a highly reproducible method to control sample preparation and nucleic acid amplification and/or detection.

It will be understood that the present invention enables the validation of the preparation and amplification and/or detection, especially for cells or biological compartments in which the release of the targeted nucleic acid is challenging. Non-limiting examples of such cells include plant cells, chloroplasts and spores.

The test sample is usually of clinical, environmental or alimentary source. In one particular embodiment, the clinical sample is a test sample chosen for example from a vaginal/anal or a nasal swab sample.

The nucleic acid amplification method is preferably PCR. Other amplification technologies including target and probe amplification methods as well as signal amplification techniques performed in liquid phase or onto solid support may also be used in accordance with the present invention. The person of ordinary skill to which the present invention pertains will adapt same to meet the particular requirements of other nucleic acid amplification methods.

In one embodiment, the amplicon detection method (e.g. the amplified product obtained following the amplification of the target sequence) is based either on hybridization of unlabeled amplicons to a labeled probe in homogeneous phase, or on hybridization of labelled amplicons to unlabeled capture probes bound onto a solid support. In another embodiment, the labels are fluorophores.

In one embodiment, the microbial cells are bacteria, fungi or parasites. In another embodiment, the microbial cells are *E. coli* cells or bacterial spores. In yet a further embodiment, the microbial cells are *Bacillus globigii* spores.

In an additional embodiment, the nucleic acid sequences serving as IC targets for nucleic acid testing assays are present on a cloning vector. In an another embodiment, the nucleic acid sequences serving as IC targets for nucleic acid testing assays are present on a plasmid vector.

In an embodiment, the test sample is of clinical or environmental, or alimentary origin.

In accordance with the present invention there is provided a reagent comprising: any one of cells, viral particles, organelles, parasites, cells comprising organelles, cells comprising viral particles, cells comprising parasites, cells comprising bacterial cells and any combination thereof, the cells, viral particles, organelles or parasites comprising at least one nucleic acid sequence serving as an internal control (IC) target for nucleic acid testing (NAT) assay; wherein the reagent is suitable to be added to a test sample undergoing sample preparation to release, concentrate and/or purify nucleic acids and amplification and/or detection of nucleic; acids so as to be used to verify: (i) the efficiency of sample preparation; and (ii) the efficiency of nucleic acid amplification and/or detection.

In accordance with the present invention, there is also provided a method for verifying the efficiency of sample preparation and the performance of nucleic acid amplification and/or detection practiced on a test sample after its preparation, the method comprising: (i) providing a reagent comprising any one of cells, viral particles, organelles, parasites, cells comprising organelles, cells comprising viral particles, cells comprising parasites, cells comprising bacterial cells and any combination thereof, the cells, viral particles, organelles or parasites comprising at least one nucleic acid sequence serving as an internal control (IC) target sample preparation and nucleic acid amplification and/or detection; (ii) adding the reagent into the test sample; (iii) submitting the test sample with the added reagent to a nucleic acid amplification procedure in order to release, the nucleic acid sequence of both the test sample and the added reagent; and (iv) submitting the released nucleic acids to further amplification and/or detection.

Other objects, advantages and features of the present invention will become more apparent upon reading of the following non restrictive description of embodiments thereof, given by way of example only with reference to the accompanying drawings.

DESCRIPTION OF ILLUSTRATIVE EMBODIMENTS

Figure 1:
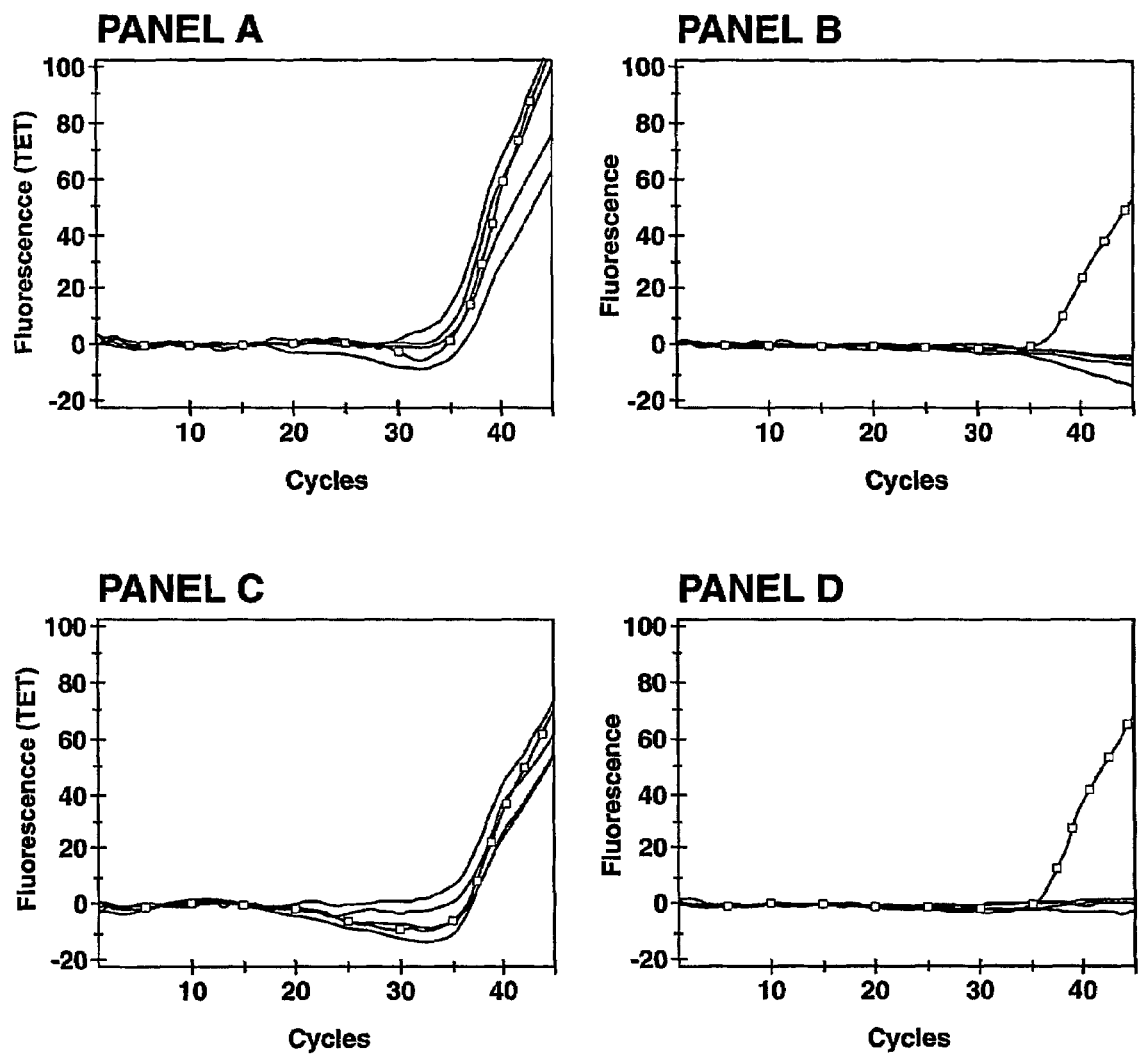
FIG. 1 shows ICSPAD versus ICAD controls in the presence of genomic DNA from *S. agalactiae*. The efficiency of amplification and detection of the ICSPAD IC template inside *E. coli* cells versus that of the purified ICAD IC template using the GBS-specific PCR assay is compared. Panel A: Four repeats of amplification and detection of 100 copies per reaction of purified and linearized recombinant plasmids carrying the IC template (i.e. ICAD controls) (straight lines). The line with white squares represents a control reaction in which the 100 copies per reaction of purified and linearized IC template were amplified and detected in the presence of 100 genome copies per reaction purified from *S. agalactiae* strain ATCC 12973. The fluorescence signal is from the TET-labeled IC-specific internal probe; Panel B: Same as Panel A except that the fluorescence signal is from the FAM-labeled GBS-specific internal probe; Panel C: Four repeats of amplification and detection of the equivalent of approximately 0.3 cell per reaction of *E. coli* containing the recombinant plasmid carrying the IC template (i.e. ICSPAD controls) (straight lines). The line with white squares represents a control reaction in which the 100 copies per reaction of purified and linearized IC template was amplified and detected in the presence of 100 genome copies per reaction purified from *Streptococcus agalactiae* strain ATCC 12973. The fluorescence signal is from the TET-labeled IC-specific probe; Panel D: Same as Panel C except that the fluorescence signal was from the FAM-labeled *S. agalactiae*-specific probe.

The present invention relates to a method (and reagents thereof) using cells, viral particles, organelles, parasites or cells comprising organelles, and/or viral particles and/or parasites, and/or bacterial cells, containing a nucleic acid sequence which serves as an IC target to verify the efficiency of (i) sample preparation for target DNA/RNA extraction, concentration and/or purification and (ii) nucleic acid amplification and/or detection. In one particular embodiment, the method comprises the following steps and elements:

1) Cells, viral particles, organelles, parasites or cells containing organelles, and/or viral particles, and/or parasites, and/or bacterial cell carrying nucleic acid sequences serving as IC targets for NAT assays are provided. The cells may be bacteria, fungi, parasites, plant or mammalian cells. In one particular embodiment, the cell is a bacterial spore. The cells, viral particles, and/or organelles, and/or parasites may be of natural origin or may be genetically engineered, to contain a chosen IC target sequence. The IC target sequences in genetically engineered cells, viruses, parasites and/or organelles may be initially cloned into a suitable cloning vector (e.g. plasmids, viruses, bacteriophages, transposons, organelle genomes) by using standard molecular biology procedures (Sambrook and Russel, 2001, Molecular Cloning: A laboratory manual (Third edition), Cold Spring Harbor Laboratory Press, New York, N.Y.; Rosenstraus et. al., 1998, J. Clin. Microbiol. 36: 191-197; Sachadyn and Kur, 1998, Molecular Cellular Probes 12: 259-262; Brightwell et al., 1998, Molecular Cellular Probes 12:367-377; Ursi et al., 1998, Molecular Cellular Probes 12: 235-238; Stocher et al., 2002, J. Virol. Methods 108:1-8). Subsequently, the recombinant vector can be incorporated into an appropriate host by using standard procedures such as transformation, electroporation, transduction or conjugation (Sambrook and Russel, 2001, Molecular Cloning: A laboratory manual (Third edition), Cold Spring Harbor Laboratory Press, New York, N.Y.).

2) The naturally-occurring or genetically modified cells, viral particles, organelles, parasites or cells comprising organelles, and/or viral particles, and/or parasites, and/or bacterial cells carrying the recombinant vector are then added to a test sample which may be of biological, environmental or alimentary origin. The cells, viruses, parasites and/or organelles are incorporated into each test sample at the appropriate concentration to obtain an efficient and reproducible amplification/detection of the IC, based on testing during the assay optimization. The optimal number of control cells added, which is dependent on the assay, is preferentially the minimal number of cells which allow to have a highly reproducible IC detection signal without having any significant detrimental effect on the amplification and/or detection of the other genetic target(s) of the nucleic acid-based assay. A sample to which are added the cells, viral particles, organelles, parasites or cells comprising organelles, and/or parasites, and/or bacterial cells, and/or viral particles, is referred to hereinbelow as a "spiked sample".

IC in PCR are usually highly purified plasmid DNA either supercoiled, or linearized by digestion with a restriction endonuclease and repurified. The inventors have noticed repeatedly (data not shown) that supercoiled IC templates are amplified much less efficiently (about 100 fold) and in a less reproducible manner than linearized and repurified IC nucleic acid templates. Consequently, ICAD controls for the present invention were all performed with linearized and repurified IC nucleic acid templates.

3) The spiked sample is then subjected to a sample preparation procedure in order to release, concentrate and/or purify nucleic acids. A variety of protocols for cell lysis and nucleic acid extraction from microbes have been described (Sambrook and Russel, 2001, Molecular Cloning: A laboratory manual (Third edition), Cold Spring Harbor Laboratory Press, New York, N.Y.; Lee et al. 1997, Nucleic Acid Amplification Technologies: Application to Disease Diagnosis, Biotechniques Books, Eaton Publishing, Boston, Mass.; Persing et al., 1993, Diagnostic Molecular Microbiology: Principles and Applications, American Society for Microbiology, Washington, D.C.; Ehrlich and Greenberg, 1994, PCR-based Diagnostics in Infectious Disease, Blackwell Scientific Publications, Boston, Mass.). These published sample preparation methods and others well-known in the art include steps for (i) concentration and/or purification of target cells, organelles, and/or viral particles, (ii) cell, organelle, and/or viral particle lysis, (iii) nucleic acid extraction, (iv) neutralization and/or inactivation of NAT inhibitors, and/or (v) nucleic acid concentration and/or purification. The inventors have also developed protocols for efficient nucleic acid extraction from a variety of clinically relevant microbial cells which are the objects of PCT patent publication WO 03/008636. Furthermore, there are many commercially available kits for nucleic acid extraction from various types of cells and viruses. PCT patent publication WO 03/008636 presents a comparison of popular commercial kits for rapid nucleic acid extraction from different microbial cultures.

4) The prepared sample is then subjected to nucleic acid amplification and/or detection performed under appropriate conditions. Amplification technologies including target and probe amplification techniques as well as signal amplification techniques performed in liquid phase or onto solid supports may be used (Nolte and Caliendo, 2003, Molecular detection and identification of microorganisms, p. 234-256, In Manual of Clinical Microbiology (8$^{th}$ ed.), Murray et al., American Society for Microbiology, Washington, D.C.; Lee et al. 1997, Nucleic Acid Amplification Technologies: Application to Disease Diagnosis, Biotechniques Books, Eaton Publishing, Boston, Mass.; Persing et al., 1993, Diagnostic Molecular Microbiology: Principles and Applications, American Society for Microbiology, Washington, D.C.; Ehrlich and Greenberg, 1994, PCR-based Diagnostics in Infectious Disease, Blackwell Scientific Publications, Boston, Mass.).

5) The efficiency of nucleic acid recovery from cells, microorganisms and/or organelles added to each test sample and/or the level of nucleic acid amplification and/or detection inhibition (if present) can be estimated by comparison with external control reaction(s). To verify the efficiency of both sample preparation and amplification and/or detection, such external control reaction(s) may be performed using a reference test sample or a blank sample spiked with cells, organelles and/or viral particles carrying the control nucleic acid sequence(s) (i.e. ICSPAD control). For example, a signal from the IC sequences present into the cells, viruses and/or organelles added to each test sample that is lower than the signal observed with the external control reaction(s) may be explained by incomplete lysis and/or inhibition of the amplification and/or detection processes for a given test sample. On the other hand, a signal from the IC sequences that is similar to the signal observed with the external control reaction(s), would confirm that the sample preparation including cell lysis is efficient and that there is no significant inhibition of the amplification and/or detection processes for a given test sample. It is also possible to verify the efficiency of nucleic acid amplification and/or detection only, by performing external control reaction(s) using highly purified control target nucleic acids added to the amplification and/or detection reaction mixture. Alternatively, verification of the efficiency of sample preparation only may be performed using external control(s) analysed by methods other than NAT (e.g. analysis using microscopy, mass spectrometry or immunological assays).

6) In one particular embodiment, the methods uses microbial cells or viral particles containing nucleic acid sequences serving as targets for an internal control (IC) in nucleic acid test (NAT) assays to verify the efficiency of cell lysis and of sample preparation as well as the performance of nucleic acid amplification and/or detection.

DEFINITIONS

In order to provide a clear and consistent understanding of terms used in the present description, a number of definitions are provided hereinbelow.

The terminology "biological compartment" is used herein to refer to the compartment which contains the nucleic acid which is targeted in the sample and which in certain embodiments, the compartment which contains the targeted internal control sequence. Non-limiting examples of such biological compartment include a membrane, a capsid, an envelope or the like, of natural origin or an engineered compartment which reflects the biological behavior of the natural biological compartment in which the targeted nucleic acid is comprised, with respect to the preparation and amplification and/or detection of the targeted nucleic acid.

The term "cell" or "cells" as used herein is used broadly and is meant to cover eukaryotic and prokaryotic cells, including for example plant cells, mammalian cells, parasites, unicellular organisms, yeasts, fungi, and bacterial cells.

The terminology "organelle", which is well-known in the art is meant to cover any cellular organelle from cells. Non-limiting examples thereof include vacuoles, mitochondria, and chloroplasts.

While the present invention is examplified using spores as a model biological compartment which is difficult to lyse (and therefore does not easily liberate a nucleic acid found therein, to be use as an amplification template), the present invention is not so limited. Indeed, the IC can be adapted to particular needs. For example, a eukaryotic cell infected with a bacteria (e.g. a mycobacteria) could be used to spike a sample prior to preparation. Cells containing organelles, or parasites could also be used to spike the sample. It will have been understood, that the present invention is more particularly useful when the biological compartment which contains the targeted nucleic acid is difficult to lyse and/or does not readily release the targeted nucleic acid for amplification. The present invention also finds advantages when the targeted nucleic acid is present in small quantities in a sample.

It should be understood that in order for the IC to validate the preparation and amplification and/or detection, in accordance with the present invention, the amplicons obtained from the targeted sample, should be distinguishable from that of the IC. In one embodiment, the primers could distinguish between the sample sequence and the control sequence. In another embodiment the primer binding sequences could be common to the targeted sample sequence and the targeted control sequence, the internal sequences between the primer binding sites, being distinguishable between the sample and control sequences. In a particular embodiment, the internal sequence in the control sequence is a genetically engineered sequence, related or not to that of the sample sequence. In one such embodiment, the same primer binding sites flank a heterogeneous sequence (which could have an enzymatic or assayable activity). In one such embodiment, the primer binding sequences used in order to detect the targeted nucleic acid in the sample, flank the beta-Gal sequence, or a smaller assayable marker. In another embodiment, the internal sequence in the internal control sequence is longer than that of the targeted sample sequence, thereby favoring the amplification of the targeted sample sequence in the sample as compared to that of the internal control, as commonly known.

The present invention also covers a spiking of a sample with a reagent which comprises more than one internal control sequence. For example, a cell, or other biological compartment, could harbor more than one IC sequence and be used to validate different preparations and amplifications and/or detections assays.

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission.

Unless defined otherwise, the scientific and technological terms and nomenclature used herein have the same meaning as commonly understood by a person of ordinary skill to which this invention pertains. Generally, the procedures for cell cultures, infection, molecular biology methods and the like are common methods used in the art. Such standard techniques can be found in reference, manuals such as for example Sambrook et al. 2001 (Molecular Cloning—A Laboratory Manual, Cold Spring Harbor Laboratories) and Ausubel et al. (1994, Current Protocols in Molecular Biology, Wiley, N.Y.).

The present description refers to a number of routinely used recombinant DNA (rDNA) technology terms. Nevertheless, definitions of selected examples of such rDNA terms are provided for clarity and consistency.

As used herein, "nucleic acid molecule", refers to a polymer of nucleotides. Non-limiting examples thereof include DNA (e.g. genomic DNA, cDNA), RNA molecules (e.g. mRNA) and chimeras thereof. The nucleic acid molecule can be obtained by cloning techniques or synthesized. DNA can be double-stranded or single-stranded (coding strand or non-coding strand [antisense]).

The term "recombinant DNA" as known in the art refers to a DNA molecule resulting from the joining of DNA segments. This is often referred to as genetic engineering. The same is true for "recombinant nucleic acid".

The term "DNA segment", is used herein, to refer to a DNA molecule comprising a linear stretch or sequence of nucleotides. This sequence when read in accordance with the genetic code, can encode a linear stretch or sequence of amino acids which can be referred to as a polypeptide, protein, protein fragment and the like.

The terminology "amplification pair" refers herein to a pair of oligonucleotides (oligos) of the present invention, which are selected to be used together in amplifying a selected nucleic acid sequence by one of a number of types of amplification processes, preferably a polymerase chain reaction. Other types of amplification processes include ligase chain reaction, strand displacement amplification, or nucleic acid sequence-based amplification, as explained in greater detail below. As commonly known in the art, the oligos are designed to bind to a complementary sequence under selected conditions.

The nucleic acid (e.g. DNA or RNA) for practicing the present invention may be obtained according to well-known methods.

Oligonucleotide probes or primers of the present invention may be of any suitable length, depending on the particular assay format and the particular needs and targeted genomes or nucleic acid employed. In general, the oligonucleotide probes or primers are at least 12 nucleotides in length, preferably between 15 and 40 nucleotides, and they may be adapted to be especially suited to a chosen nucleic acid amplification system. As commonly known in the art, the oligonucleotide probes and primers can be designed by taking into consideration the melting point of hybridization thereof with its targeted sequence (see below and in Sambrook et al., 2001 supra; Ausubel et al., 1989, in Current Protocols in Molecular Biology, John Wiley & Sons Inc., N.Y.). In one particular embodiment, the primers used serve to amplify the targeted nucleic acid as well as the IC nucleic acid. It will be understood that the amplified sequences or the means to detect them should enable a distinction between the targeted nucleic acid of the sample and that of the IC.

The term "DNA" molecule or sequence (as well as sometimes the term "oligonucleotide") refers to a molecule comprised generally of the deoxyribonucleotides adenine (A), guanine (G), thymine (T) and/or cytosine (C). The term "oligonucleotide" or "DNA" can be found in linear DNA molecules or fragments, viruses, plasmids, vectors, chromosomes or synthetically derived DNA. Particular double-stranded DNA sequences may be described according to the normal convention of giving only the sequence in the 5' to 3' direction.

"Nucleic acid hybridization" refers generally to the hybridization of two single-stranded nucleic acid molecules having complementary base sequences, which under appropriate conditions will form a thermodynamically favored double-stranded structure. Examples of hybridization conditions can be found in the two laboratory manuals referred above (Sambrook et al., 2001, supra and Ausubel et al., 1989, supra) and are commonly known in the art. In the case of a hybridization to a nitrocellulose filter, as for example in the well known Southern blotting procedure, a nitrocellulose filter can be incubated overnight at 65° C. with a labeled probe in a solution containing, high salt (5×SSC or 5×SSPE), 5×Denhardt's solution, 1% SDS, and 100 µg/ml denatured carrier DNA (e.g. salmon sperm DNA). Another high stringency conditions uses the same solution comprising 50% formamide and incubated at 42° C. The non-specifically binding probe can then be washed off the filter by several washes in 0.2×SSC/0.1% SDS at a temperature which is selected in view of the desired stringency: room temperature (low stringency), 42° C. (moderate stringency) or 65° C. (high stringency). The selected temperature is based on the melting temperature (Tm) of the DNA hybrid. Of course, RNA-DNA hybrids can also be formed and detected. In such cases, the conditions of hybridization and washing can be adapted according to well known methods by the person of ordinary skill. Stringent conditions will be preferably used (Sambrook et al., 2001, supra).

Probes of the invention can be utilized with naturally occurring sugar-phosphate backbones as well as modified backbones including phosphorothioates, dithionates, alkyl phosphonates and α-nucleotides and the like. Modified sugar-phosphate backbones are generally taught by Miller, 1988, Ann. Reports Med. Chem. 23:295 and Moran et al., 1987, Nucleic Acids Res., 14:5019. Probes of the invention can be constructed of either ribonucleic acid (RNA) or deoxyribonucleic acid (DNA), and preferably of DNA.

The types of detection methods in which probes can be used include Southern blots (DNA detection), dot or slot blots (DNA, RNA), and Northern blots (RNA detection). Labeled proteins could also be used to detect a particular nucleic acid sequence to which it binds. Other detection methods include kits containing probes on a dipstick setup and the like.

Although the present invention is not specifically dependent on the use of a label for the detection of a particular nucleic acid sequence, such a label might be beneficial, in certain embodiments for increasing the sensitivity of the detection. Furthermore, it can enable automation. Probes can be labeled according to numerous well-known methods (Sambrook et al., 1989, supra). Non-limiting examples of labels include $^{3}H$, $^{14}C$, $^{32}P$, and $^{35}S$. Non-limiting examples of detectable markers include ligands, fluorophores, chemiluminescent agents, enzymes, and antibodies. Other detectable markers for use with probes, which can enable an increase in sensitivity of the method of the invention, include biotin and radionucleotides. It will become evident to the person of ordinary skill that the choice of a particular label dictates the manner in which it is bound to the probe.

As commonly known, radioactive nucleotides can be incorporated into probes of the invention by several methods. Non-limiting examples thereof include kinasing the 5' ends of the probes using gamma $^{32}P$ ATP and polynucleotide kinase, using the Klenow fragment of Pol I of E. coli in the presence of radioactive dNTP (e.g. uniformly labeled DNA probe using random oligonucleotide primers in low-melt gels), using the SP6/T7 system to transcribe a DNA segment in the presence of one or more radioactive NTP, and the like.

As used herein, "oligonucleotides" or "oligos" define a molecule having two or more nucleotides (ribo or deoxyribonucleotides). The size of the oligo will be dictated by the particular situation and ultimately on the particular use thereof and adapted accordingly by the person of ordinary skill. An oligonucleotide can be synthesized chemically or derived by cloning according to well known methods. While they are usually in a single-stranded form, they can be in a double-stranded form and even contain a "regulatory region".

As used herein, a "primer" defines an oligonucleotide capable of annealing to a target sequence, (whether from the sample or from the chosen internal control) thereby creating a double stranded region which can serve as an initiation point for DNA synthesis under suitable conditions. Primers can be, for example, designed to be specific for certain alleles, for certain strains, or for certain species so as to be used in an allele-specific amplification system, species-specific, or strain-specific system. In addition, the primers can be chosen to be more universal. In accordance with the present invention, primers can be chosen so as to enable multiplex amplifications. In accordance with one embodiment of the present invention, the use of such a primer with the other necessary reagents would give rise to an amplification product only when the allele-, species-, or strain-specific sequence which is targeted, is present in the sample.

Amplification of a selected, or target, nucleic acid sequence may be carried out by a number of suitable methods. See generally Kwoh et al., 1990, Am. Biotechnol. Lab. 8:14-25. Numerous amplification techniques have been described and can be readily adapted to suit particular needs of a person of ordinary skill. Non-limiting examples of amplification techniques include polymerase chain reaction (PCR), ligase chain reaction (LCR), strand displacement amplification (SDA), transcription-based amplification, the Qβ replicase system and NASBA (Kwoh et al., 1989, Proc. Natl. Acad. Sci. USA 86, 1173-1177; Lizardi et al., 1988, BioTechnology 6:1197-1202; Malek et al., 1994, Methods Mol. Biol., 28:253-260; and Sambrook et al., 1989, supra). Preferably, amplification will be carried out using PCR.

Polymerase chain reaction (PCR) is carried out in accordance with known techniques. See, e.g., U.S. Pat. Nos. 4,683,195; 4,683,202; 4,800,159; and 4,965,188 (the disclosures of all three U.S. Patent are incorporated herein by reference). In general, PCR involves, a treatment of a nucleic acid sample (e.g., in the presence of a heat stable DNA polymerase) under hybridizing conditions, with one oligonucleotide primer for each strand of the specific sequence to be detected. An extension product of each primer which is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample is analyzed to assess whether the sequence or sequences to be detected are present. Detection of the amplified sequence may be carried out by visualization following EtBr staining of the DNA following gel electrophores, or using a detectable label in accordance with known techniques, and the like. For a review on PCR techniques (see PCR Protocols, A Guide to Methods and Amplifications, Michael et al. Eds, Acad. Press, 1990).

Ligase chain reaction (LCR) is carried out in accordance with known techniques (Weiss, 1991, Science 254:1292). Adaptation of the protocol to meet the desired needs can be carried out by a person of ordinary skill. Strand displacement amplification (SDA) is also carried out in accordance with known techniques or adaptations thereof to meet the particular needs (Walker et al., 1992, Proc. Natl. Acad. Sci. USA 89:392-396; and ibid., 1992, Nucleic Acids Res. 20:1691-1696).

It will be readily recognized by the person of ordinary skill, that the nucleic acid sequence of the present invention can be incorporated into anyone of numerous established kit formats which are well known in the art.

A "heterologous" (e.g. a heterologous gene or sequence) region of a DNA molecule is a subsegment of DNA within a larger segment that is not found in association therewith in nature. The term "heterologous" can be similarly used to define two polypeptidic segments not joined together in nature.

The term "vector" is commonly known in the art and defines a plasmid DNA, phage DNA, viral DNA and the like, which can serve as a DNA vehicle into which DNA of the present invention can be cloned. Numerous types of vectors exist and are well known in the art.

The term "expression" defines the process by which a gene is transcribed into mRNA (transcription). The mRNA can then be translated (translation) into one polypeptide (or protein) or more.

The terminology "expression vector" defines a vector or vehicle as described above but designed to enable the expression of an inserted sequence following transformation into a host. The cloned gene (inserted sequence) is usually placed under the control of control element sequences such as promoter sequences. The placing of a cloned gene under such control sequences is often referred to as being operably linked to control elements or sequences.

Operably linked sequences may also include two segments that are transcribed onto the same RNA transcript. Thus, two sequences, such as a promoter and a "reporter sequence" are operably linked if transcription commencing in the promoter will produce an RNA transcript of the reporter sequence. In order to be "operably linked" it is not necessary that two sequences be immediately adjacent to one another.

Expression control sequences will vary depending on whether the vector is designed to express the operably linked gene in a prokaryotic or eukaryotic host or both (shuttle vectors) and can additionally contain transcriptional elements such as enhancer elements, termination sequences, tissue-specificity elements, and/or translational initiation and termination sites.

"Promoter" refers to a DNA regulatory region capable of binding directly or indirectly to RNA polymerase in a cell and initiating transcription of a downstream (3' direction) coding sequence. For purposes of the present invention, the promoter is preferably bound at its 3' terminus by the transcription initiation site and extends upstream (5' direction) to include the minimum number of bases or elements necessary to initiate transcription at levels detectable above background. Within the promoter will be found a transcription initiation site (conveniently defined by mapping with S1 nuclease), as well as protein binding domains (consensus sequences) responsible for the binding of RNA polymerase. Eukaryotic promoters will often, but not always, contain "TATA" boxes and "CCAT" boxes. Prokaryotic promoters contain −10 and −35 consensus sequences, which serve to initiate transcription and the transcript products contain Shine-Dalgarno sequences, which serve as ribosome binding sequences during translation initiation.

The term "allele" defines an alternative form of a gene which occupies a given locus on a chromosome. As commonly known, a "mutation" is a detectable change in the genetic material which can be transmitted to a daughter cell. As well known, a mutation can be, for example, a detectable change in one or more deoxyribonucleotide. For example, nucleotides can be added, deleted, substituted for, inverted, or transposed to a new position. Spontaneous mutations and experimentally induced mutations exist. A mutant polypeptide can be encoded from this mutant nucleic acid molecule.

As used herein, the term "purified" refers to a molecule having been separated from a cellular component. Thus, for example, a "purified nucleic acid" has been purified to a level not found in nature. A "substantially pure" molecule is a molecule that is lacking in most other cellular components.

A host cell or indicator cell has been "transfected" by exogenous or heterologous DNA (e.g. a DNA construct) when such DNA has been introduced inside the cell. The transfecting DNA may or may not be integrated (covalently linked) into chromosomal DNA making up the genome of the cell. In prokaryotes, yeast, and mammalian cells for example, the transfecting DNA may be maintained on a episomal element such as a plasmid. With respect to eukaryotic cells, a stably transfected cell is one in which the transfecting DNA has become integrated into a chromosome so that it is inherited by daughter cells through chromosome replication. This stability is demonstrated by the ability of the eukaryotic cell to establish cell lines or clones comprised of a population of daughter cells containing the transfecting DNA. Transfection methods are well known in the art (Sambrook et al., 2001, supra; Ausubel et al., 1994 supra).

The present invention relates to a kit which enables the validation of results obtained following an amplification of a targeted nucleic acid in a sample. For example, a compartmentalized kit in accordance with the present invention includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample (DNA, RNA or cells or other biological compartments), a container which contains the primers used in the assay, containers which contain enzymes, containers which contain wash reagents, and containers which contain the reagents used to detect the extension products. Of course, the specific choice of containers can be adapted by the person of ordinary skill to which the invention pertains. Such person of ordinary skill can adapt the kit to meet particular needs (e.g. type of amplification method, type of targeted nucleic acid, type of cells, etc.).

This invention will be described hereinbelow by way of specific examples and embodiments and accompanying FIGS. 1 to 7, the purpose of which being to illustrate the invention rather than to limit its scope.

EXAMPLE 1

Cellular ICSPAD using E. coli Cells Applied to the Detection of Group B Streptococci from Vaginal/Anal Swabs Streptococcus agalactiae, the Group B streptococcus (GBS), is responsible for a severe illness affecting neonate infants. The bacterium is passed from the healthy carrier mother to the baby during delivery. To prevent this infection, it is recommended to treat expectant mothers susceptible of carrying GBS in their vaginal/anal flora. Carrier status is often a transient condition and rigorous monitoring requires culture-based classic bacterial identification weeks before delivery. To improve the detection and identification of GBS the inventors have developed a specific and sensitive PCR test which is rapid enough to be performed at delivery (Ke et al., 2000, Clin. Chem. 46:324-331; Bergeron et al., 2000, New Engl. J. Med. 343:175-179).

Clinical specimens. Vaginal/anal swabs were collected from consenting pregnant women admitted for delivery at the Centre Hospitalier Universitaire de Québec, Pavilion Saint-Francois d'Assise, following the Centers for Disease Control and Prevention (CDC) recommendations. The samples were obtained either before or after rupture of amniotic membranes. The swab samples were tested by PCR and culture at the Centre de Recherche en Infectiologie de l'Université Laval within 24 hours after collection. The investigation was approved by the Ethic Committee of Clinical Research of the Centre Hospitalier Universitaire de Québec, Pavilion Saint-François d'Assise, and all participants gave informed consent.

Bacterial culture. An overnight culture of E. coli INVαF (Invitrogen) transformed with a recombinant plasmid pCR2.1 (Invitrogen) carrying a DNA insert serving as template for the IC was grown in Luria-Bertani (LB) broth supplemented with 50 µg/mL of kanamicin. Subsequently, 40 µL of the overnight culture was used to inoculate 3 mL of fresh LB with kanamicin and incubated at 35° C. with agitation until the culture reached the mid-log phase of growth ($OD_{600}$ of around 0.5). In order to estimate the number of colony forming units (CFU), 1:10 serial dilutions in 0.01 M phosphate-buffered saline, pH 7.4 (Sigma) of the mid-log culture were plated onto blood agar and incubated 1 to 2 days at 35° C. for CFU count determinations.

Rapid DNA extraction. Upon reception, the swabs were processed prior to PCR amplification following a rapid DNA extraction procedure described in PCT patent publication WO 03/008636. In brief 50 µL of the swab suspension or 100 µL of a diluted mid-log bacterial culture (E. coli carrying the IC template DNA into pCR2.1) equivalent to the turbidity of a 0.5 McFarland standard was transferred to a 1.5-mL, screw-capped microtube containing 0.05 g of sterile, acid-washed glass beads. Two sizes of beads, the first ranging from 150 to 212 µm and the second from 710 to 1180 µm were mixed in a 4:1 ratio. The microtube was vortexed at maximum speed for 5 min on a GENIE2™ model vortex (Fisher Scientific). After a quick centrifuge spin, the microtube was heated for 2 min at 95° C.

Oligonucleotides. Two GBS-specific PCR primers (Sag59: 5'-TTTCACCAGCTGTATTAGAAGTA-3' (SEQ ID NO: 1) and Sag190: 5'-GTTCCCTGAACATTATCTTT GAT-3' (SEQ ID NO: 2) described in Ke et al., 2000, Clin. Chem. 46:324-331 and corresponding respectively to SEQ ID NOs 9 and 10 of patent publication WO 98/20157) targetting the cfb gene encoding the CAMP factor (a diffusible extracellular protein of S. agalactiae) were used. A 180-bp DNA fragment cloned into the plasmid pCR2.1 was used as a template for the IC (Ke et al., 2000, Clin. Chem. 46:324-331). The 180-bp fragment consists of a 134-bp sequence not found in GBS flanked by the sequence of each of the two GBS-specific primers. Two molecular beacons (5'-FAM -CCACGC-CCCAGCAAATGGCTCAAAAGCGCGTGG-DABCYL-3' (SEQ ID NO: 3) hybridizing to GBS-specific amplicons and 5'-TET -CCACGCGAAAGGTGGAGCAATGTGAAG-GCGTGG-DABCYL-3' (SEQ ID NO: 4) hybridizing to the IC amplicons) were synthesized and HPLC-purified by Biosearch Technologies Inc.

PCR amplification. Real-time PCR amplifications were performed either from purified genomic DNA prepared by using the GNOME™ DNA isolation kit (Qbiogen) or directly from vaginal/anal specimens. Amplification reactions were performed in a 25 µL reaction mixture containing 50 mM Tris-HCl (pH 9.1), 16 mM ammonium sulfate, 8 mM $MgCl_2$, 0.4 µM of primer Sag59 and 0.8 µM of primer Sag190, 0.2 µM of the GBS-specific molecular beacon, 0.4 µM of the IC molecular beacon, 200 µM each of the four deoxynucleoside triphosphates, 450 µg/mL bovine serum albumine, 1.25 unit of Klentaq1™ DNA polymerase (AB Peptides) combined with TAQSTART™ Taq polymerase antibody (BD Biosciences) and the IC template. The IC template used in PCR amplifications was either (i) on a recombinant plasmid into E. coli INVαF™ (Invitrogen) cells in the mid-log phase of growth at the equivalent of approximately 0.3 E. coli cells per PCR reaction to provide an ICSPAD control or (ii) in the same recombinant plasmid purified and linearized by digestion with EcoRI at 100 copies per PCR reaction as previously described to provide an ICAD control (Ke et al., 2000, Clin. Chem. 46:324-331). Reaction mixtures were subjected to thermal cycling (3 min at 94° C., and then 45 cycles of 5 sec at 95° C. for the denaturation step, 14 sec at 56° C. for the annealing step, and 5 sec at 72° C. for the extension step) using a SMART CYCLER™ PCR instrument (Cepheid). The GBS-specific and IC-specific amplification/detection was monitored in real-time by measuring the fluorescence signal at every PCR cycle.

Results and Discussion

The specificity of the assay demonstrated that only DNA from GBS strains could be amplified. The GBS-specific real-time PCR assay did not amplify DNAs from any other bacterial species tested including 14 streptococcal species other than GBS (Ke et al., 2000, Clin. Chem. 46:324-331). The sensitivity of the assay was in the range of 1 to 10 genome copies of GBS per PCR reaction from various serotypes thereby confirming the high sensitivity and the ubiquity of the GBS-specific PCR assay. The inventors have demonstrated that this assay is suitable for rapid (around 45 min) detection of GBS directly from vaginal/anal swabs from pregnant women at the time of delivery (Bergeron et al., 2000, New Engl. J. Med. 343:175-179).

Figure 2:
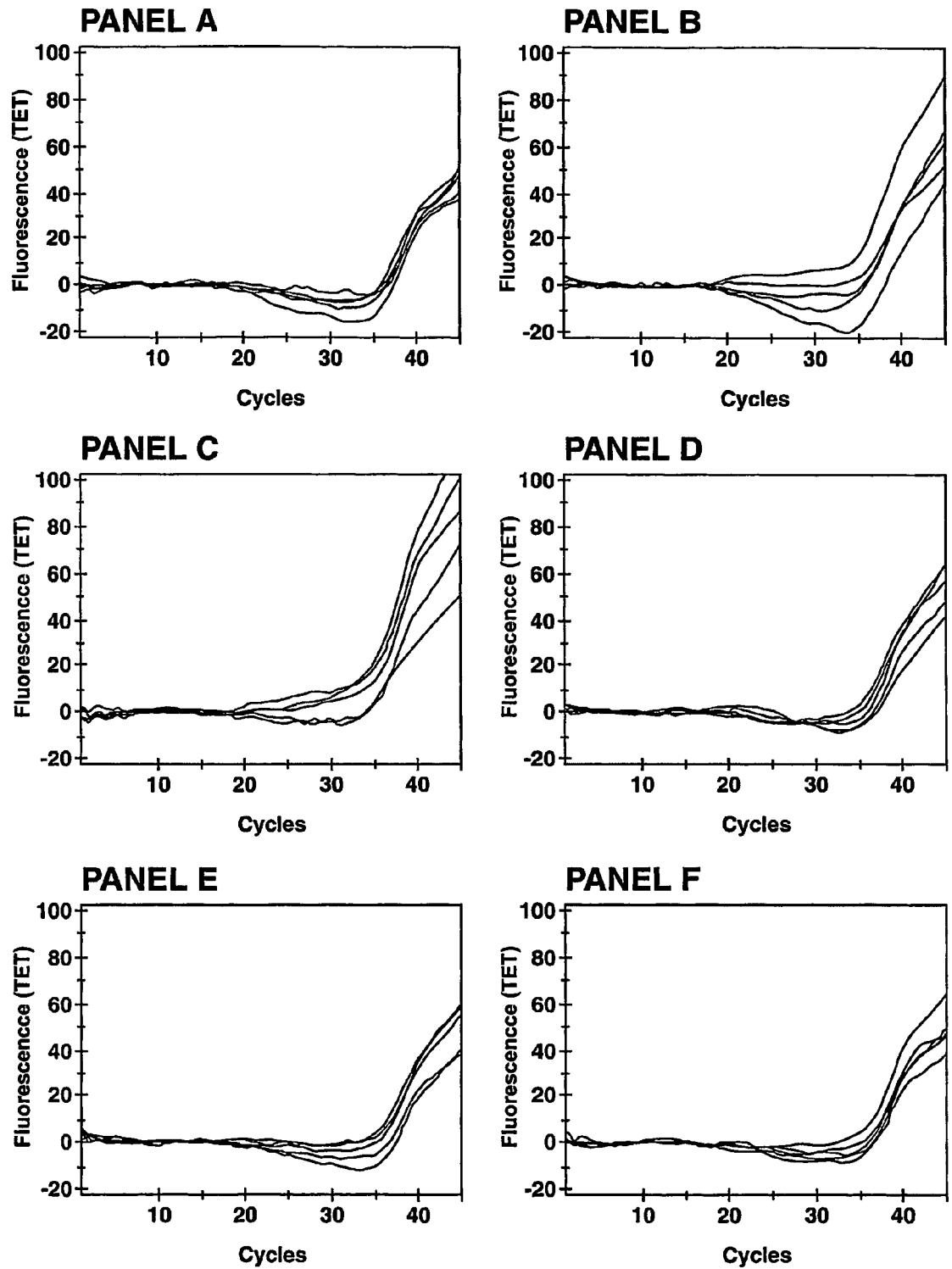
FIG. 2 shows ICSPAD versus ICAD controls in the presence of vaginal/anal sample negative for GBS. The efficiency of amplification and detection of the ICSPAD IC template inside *E. coli* cells versus that of the purified ICAD IC template using the GBS-specific PCR assay is compared. All assays were performed in the presence of a vaginal/anal sample negative for GBS which was collected from a pregnant woman at delivery. Panels A, C and E: Five repeats of amplification and detection of 100 copies per reaction of purified and linearized recombinant plasmids carrying the IC template (i.e. ICAD controls) in the presence of a prepared GBS-negative vaginal/anal sample (sample #2417 for Panel A; sample #2256 for Panel C; sample #2290 for Panel E). The fluorescence signal is from the TET-labeled IC-specific probe. Panels B, D, and F: Same as Panels A, C and E except that the amplification and detection of the IC was from the equivalent of approximately 0.3 cell per reaction of *E. coli* containing the recombinant plasmid carrying the IC template (i.e. ICSPAD controls).
Figure 3:
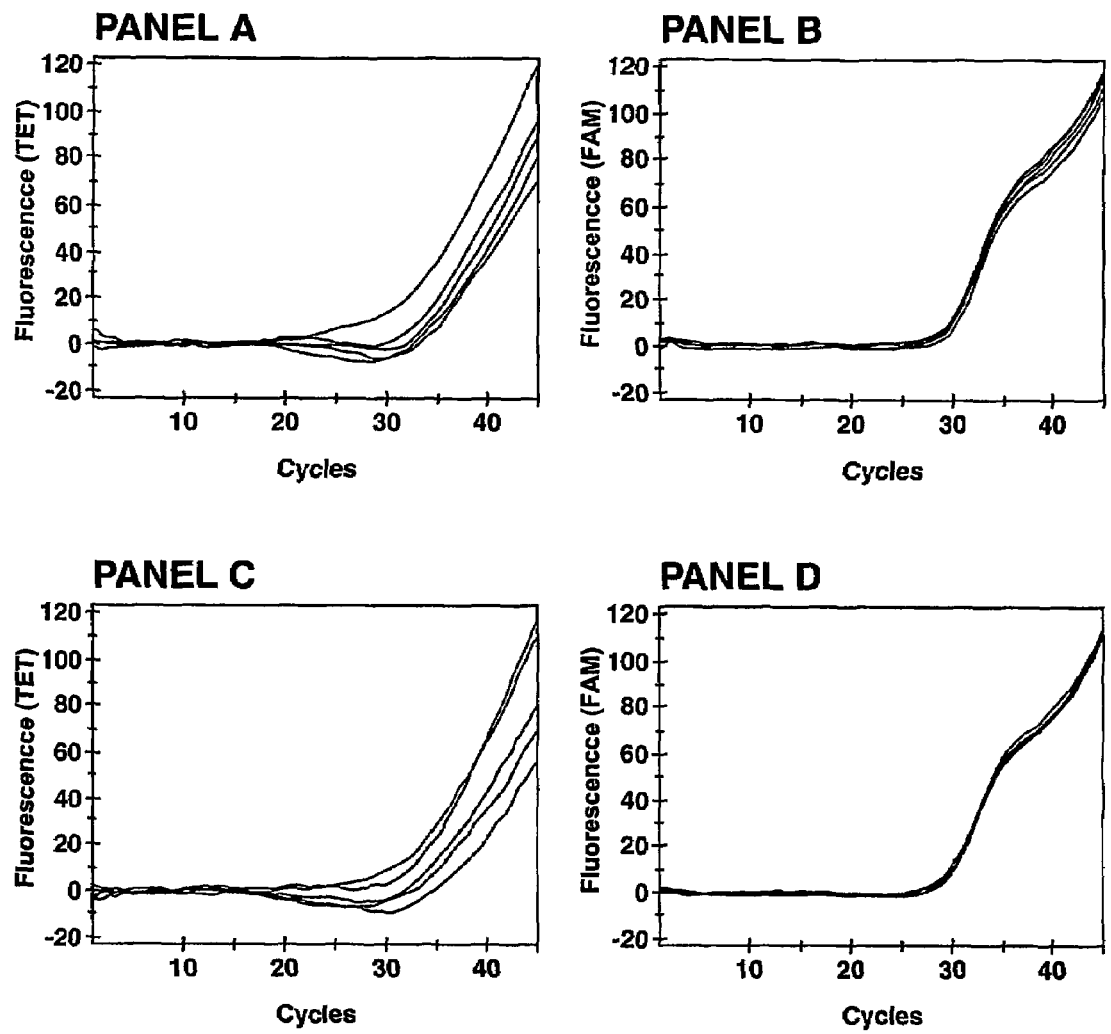
FIG. 3 shows ICSPAD versus ICAD controls in the presence of vaginal/anal sample positive for GBS. The efficiency of amplification and detection of the ICSPAD IC template inside *E. coli* cells versus that of the purified ICAD IC template using the GBS-specific PCR assay is compared. All assays were performed in the presence of a vaginal/anal sample positive for GBS which was collected from a pregnant woman at delivery. Panel A: Five repeats of amplification and detection of 100 copies per reaction of purified and linearized recombinant plasmids carrying the IC template (i.e. ICAD controls) in the presence of the prepared GBS-positive vaginal/anal sample #2416. The fluorescence signal is from the TET-labeled IC-specific probe. Panel B: Same as Panel A except that the fluorescence signal is from the FAM-labeled *S. agalactiae*-specific probe. Panel C: Five repeats of amplification and detection of the equivalent of approximately 0.3 cell per reaction of *E. coli* containing the recombinant plasmid carrying the IC template (i.e. ICSPAD controls) in the presence of the GBS-positive vaginal/anal sample #2416. The fluorescence signal is from the TET-labeled IC-specific probe. Panel D: Same as Panel C except that the fluorescence signal is from the FAM-labeled *S. agalactiae*-specific probe.

In order to evaluate the use of *E. coli* INVαF cells containing the recombinant plasmid carrying the IC DNA template to provide an ICSPAD control, we have compared the amplification/detection efficiency by the GBS-specific PCR assay of *E. coli* cells containing the IC with that of the IC template present on the same recombinant plasmid purified and linearized added to the amplification/detection reaction mixture (FIG. 1). Comparison of the performance of the cellular versus purified IC template in the presence of genomic DNA purified from GBS showed that the performance of these two IC methods was similar. Testing with vaginal/anal samples, collected from pregnant women at delivery and prepared for PCR as previously described (Bergeron et al., 2000, New Engl. J. Med. 343:175-179; PCT patent publication WO 03/008636), also showed that amplification of the IC control templates present into *E. coli* cells (i.e. ICSPAD control) had a reproducibility comparable to that of purified IC templates (i.e. ICAD control) and that there was no significant detrimental effect on the performance of the GBS-specific PCR assay (FIGS. 2 and 3). On average, the equivalent of approximately 0.3 cell of *E. coli* in the mid-log phase of growth per PCR reaction was found to be optimal as it did not interfere with GBS detection and yielded reproducible IC amplifications. The efficiency of PCR amplification of the ICSPAD IC template present into *E. coli* cells appeared to be similar to that of the purified and linearized plasmid carrying the ICAD IC template (100 copies per reaction). This analysis is based on the fact that there is approximately 500 copies of plasmid pCR2.1 (derived from pUC replicons) per *E. coli* cell (Sambrook and Russel, 2001, Molecular Cloning: A laboratory manual (Third edition), page 1.4, Cold Spring Harbor Laboratory Press, New York, N.Y.).

Surprisingly, amplification/detection of the IC template present on a plasmid inside *E. coli* cells was more efficient and more reproducible than that of the same plasmid purified in its supercoiled form. For the present GBS assay, amplification of the supercoiled IC plasmid was shown to be approximately 100-fold less efficient and less reproducible than amplification of the same plasmid linearized (data not shown). The inventors had similar findings using several other PCR assays. The explanation for the highly efficient and reproducible amplification of the supercoiled plasmid inside microbial cells is unknown. Clearly, it provides several advantages over commonly used purified IC templates by preventing the need to purify plasmidic DNA and digest it with a restriction endonuclease for linearization.

In conclusion, ICSPAD controls provided by using *E. coli* cells containing a recombinant plasmid carrying an IC nucleic acid template added to the test sample prior to its preparation for PCR are as efficient and as reproducible as the ICAD controls using highly purified IC nucleic acid templates incorporated directly into the amplification/detection reaction mixture. The main advantage of incorporating the IC nucleic acid templates into bacterial cells (i.e. ICSPAD control) is that it allows a validation of both the sample preparation method and the amplification and/or detection processes because amplification of the IC template is often dependent on the efficiency of the sample preparation protocol to (i) lyse the bacterial cells containing the IC template, (ii) release the nucleic acids for amplification and/or detection and (iii) eliminate, inactivate and/or neutralize amplification and/or detection inhibitors found in test samples. Of course as described above, the instant invention is not limited to bacterial cells containing the IC template. Indeed any virus, parasite or organelle can be used in accordance with the present invention. The present invention finds a particular utility when the targeted nucleic acid in a sample is challenging to extract and/or purify and/or liberate from the environment in which it is found. Thus, a nucleic acid target serving as an IC for both extraction and/or preparation, and/or purification, and/or liberation (which defines what is meant herein by preparation) to enable its amplification and serve for a control for amplification and/or detection and preparation, which better reflects the conditions of the tested sample is provided by the instant invention. The present invention is of particular relevance when the targeted nucleic acid is found in minimal amount in a sample. The present invention provides the means to control for the preparation and amplification and/or detection of a targeted nucleic acid present in less than 100 copies of a genome per PCR reaction, or 40 copies or less than 20 copies per PCR reaction or other amplification method. In one particular embodiment the present invention provides the means to control for the preparation and amplification and/or detection of a targeted nucleic acid present in 1-20 or even 1-10 copies of genome per PCR reaction.

It will understood that many other ways to perform the present method are possible. The sample preparation method may also include (i) concentration and/or purification of target cells prior to lysis, and/or (ii) nucleic acid concentration and/or purification. In this example, we have selected a control gene which permitted the use of a minimal number of primers. Indeed, in this case, the probes discriminate between the IC target and the target of interest. Other genes and primers derived therefrom may be used; in so far as the primers present in an amplification mixture can anneal to their DNA targets under the same conditions, any control nucleic acids (i.e. IC) different from the nucleic acids of interest may also be used.

EXAMPLE 2

Preparation of *Bacillus globigii* Spores

*Bacillus globigii* spores were generated in a sporulation agar medium composed of the following reagents (by liter of solution): 5 g peptone, 3 g beef extract, 5 mg manganese sulfate, and 15 g agar, final pH 6.8 at 25° C. *B. globigii* cells were first grown overnight at 35° C. on blood agar (tryptone soy agar plus 5% sheep blood). The sporulation agar medium was then inoculated with colonies from the blood agar and incubated overnight at 35° C., followed by an incubation at room temperature for 10 days. Subsequently, the level of sporulation was evaluated using a Petroff-Hausser counting chamber.

Bacterial colonies, consisting of approximately 90% spores and 10% vegetative cells, were resuspended in 1 mL of 1% Triton X-100™ by vortexing vigorously for 2 min. Cells were centrifuged for 2 min at 10000 g. After discarding the supernatant, the cell pellet was washed once in 1% Triton X-100 by vortexing vigorously for 2 min. Cells were then centrifuged again as described above. After discarding the supernatant, the cell pellet was resuspended in 1 mL of ultra-pure sterile water by vortexing vigorously for 2 min. The cell suspension was submitted to a heat treatment (80° C. for 30 min). Cells were centrifuged as described above and the pellet was washed twice in 1 mL of ultra-pure sterile water, each wash being centrifuged also as described above. The final pellet was resuspended in 1 mL of ultra-pure water. Subsequently, 200 µL of spore suspension were submitted to buoyant density separation over 4 mL of a solution containing 0.8 g/mL of sucrose and 0.5% Triton X-100 in a 15 mL screw-capped tube. The mixture was centrifuged 5 min at 850 g and then 500 µL of the supernatant was transferred to a 1.5 mL screw-cap tube. After a centrifugation of 2 min at 10000 g, the supernatant was removed and the cell pellet was washed twice in 1 mL of ultra-pure water, each wash being centrifuged as described above. Finally, the pellet was resuspended in 1 mL of ultra-pure water. The final purified spore suspension was diluted 1:10 in ultra-pure water and placed in a Petroff-Hausser counting chamber for spore count.

EXAMPLE 3

Use of ICSPAD IC Template Naturally Found in *B. globigii* Applied to the Detection of Methicillin-Resistant *S. aureus* from Nasal Swabs

*Staphylococcus aureus* is a major pathogen causing a wide spectrum of clinical manifestations, such as wound infections, pneumonia, septicemia, and endocarditis. Beta-lactam antimicrobial agents are the preferred drugs for serious *S. aureus* infections. However, since the introduction of methicillin into clinical use, methicillin-resistant *S. aureus* (MRSA) strains have emerged worldwide as important nosocomial pathogens and the prevalence of these strains in the community is now increasing substantially.

The inventors have developed a real-time multiplex PCR assay useful for the detection of MRSA directly from specimens containing a mixture of staphylococci (PCT patent publication PCT/CA02/00824). This assay comprises a primer targetting type iv SCCmec right extremity sequences used in combination with a primer and a molecular beacon probe specific to the *S. aureus* chromosomal orfX gene located at the right of the SCCmec integration site. This real-time PCR assay was validated using a variety of Gram-negative and Gram-positive bacterial species, as well as many staphylococcal strains from various countries (PCT patent publication PCT/CA02/00824). The assay was also used to detect MRSA directly from nasal specimens.

Clinical samples. Nasal swabs were collected from volunteers at the Centre Hospitalier Universitaire de Québec (Pavillon CHUL) in Quebec City. Nasal specimens were collected with a collection and transport system for aerobes (Venturi Transystem, Copan). A swab was carefully inserted in each nostril and gently rotated. Swab was inserted into the transport medium immediately after obtention of the sample. The swab samples were resuspended in 1 mL of a buffer containing 10 mM Tris, 1 mM EDTA and 1.5 mg/mL BSA (TEB buffer) by vortexing vigorously for 1 min. The samples were then stored frozen at −20° C. until use.

Bacterial culture. An overnight culture of *Staphylococcus aureus* ATCC 33592 in LB broth was prepared. Subsequently, 100 µL of the overnight culture was used to inoculate 10 mL of fresh LB and incubated at 35° C. with agitation until the culture reach the mid-log phase of growth ($OD_{600}$ of around 0.5). CFU count determinations were performed as described in Example 1.

Sample preparation. The nasal swabs were processed prior to PCR amplification following a rapid DNA extraction procedure described in PCT patent publication WO 03/008636. In brief, 50 µL of the swab suspension was transferred to a 1.5-mL, screw-capped microtube containing acid-washed glass beads (see Example 1). Then, approximately 13500 *B. globigii* spores prepared as described in Example 2, were used to spike each nasal specimen. Subsequently, either $1\times10^3$, $1\times10^4$, or no *Staphylococcus aureus* cells in mid-log phase of growth were also added to the nasal specimens in a final volume of 70 µL. The microtube was vortexed at maximum speed for 5 min on a GENIE2™ model vortex (Fisher Scientific). After a quick centrifuge spin, the microtube was heated for 2 min at 95° C.

Internal controls (IC). A 324-bp DNA fragment cloned into the plasmid pCR2.1 was used as a template for the IC (Ke et al., 2000, Clin. Chem. 46:324-331). The cloned fragment consists of a 276-bp sequence not found in MRSA flanked by the sequence of each of the two MRSA-specific primers. The performance of this plasmidic ICAD was compared with that of the ICSPAD method using *B. glogigii* spores prepared as described in Example 2.

PCR amplification. Real-time PCR amplifications were performed directly from nasal specimens. Amplification reactions were performed in a 25 µL reaction mixture containing 10 mM Tris-HCl (pH 9.0), 50 mM potassium chloride, 0.1% Triton, 3.45 mM $MgCl_2$, 0.4 µM of primers XSau325 (5'-GGATCAAACGGCCTGCACA-3'; SEQ ID NO: 5) and mec1V511 (5'-CAAATATTATCTCGTAATTTACCT-TGTTC-3'; SEQ ID NO: 6) targetting the SCCmec right extremity junction (MREJ) type iv, 0.2 µM of primers ABgl158 (5'-CACTTCATTTAGGCGACGATACT-3'; SEQ ID NO: 7) and ABgl345a (5'-TTGTCTGTGAATCG-GATCTTTCTC-3'; SEQ ID NO: 8) targetting the *B. globigii* atpD gene encoding the ATPase, 0.1 µM of the MRSA-specific (5'-FAM -CGTCTTACAACGCAGTAACTACGCAC-TATCATTCAOC-BHQ-1-3'; SEQ ID NO: 9) TaqMan fluorescent probe, either 0.1 µM of the *B. globigii*-specific the TaqMan fluorescent probe (5'-TET -CGTCCCAATGTTA-CATTACCAACCGGCACTOAAATAGG-BHQ-1-3'; SEQ ID NO: 10) or the fluorescent probe targeting the purified and linearized recombinant plasmid (5'-TET -ATGCCTCTTCA-CATTOCTCCACCTTTCCTGTG-BHQ-1-3'; SEQ ID NO: 11), 200 µM each of the four deoxynucleoside triphosphates, 340 µg/mL bovine serum albumine, 0.035 U of Taq DNA polymerase (Promega) combined with TAQSTART™ Taq polymerase antibody (BD Biosciences), 100 copies of the purified and linearized recombinant plasmid carrying the IC template and 2.5 µL of nasal specimen spiked with bacterial spores as described above. Reaction mixtures were subjected to thermal cycling (3 min at 95° C., and then 48 cycles of 5 sec at 95° C. for the denaturation step, 15 sec at 60° C. for the annealing step, and 15 sec at 72° C. for the extension step) using a SMART CYCLER™ PCR machine (Cepheid). The MRSA-specific and IC-specific amplifications/detections were monitored in real-time by measuring the fluorescence signal at every PCR cycle.

Results and Discussion

Figure 4:
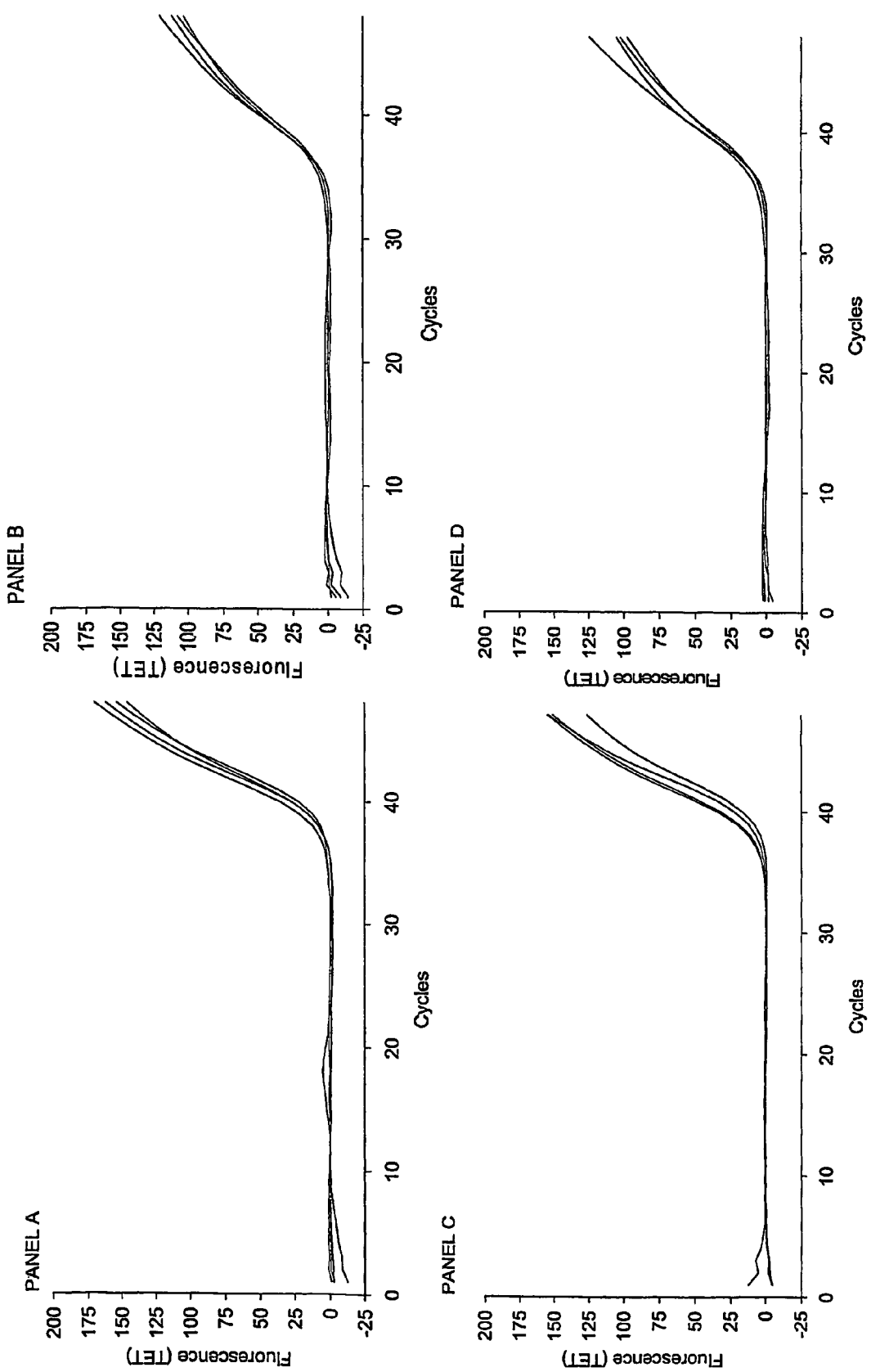
FIG. 4 shows ICSPAD versus ICAD controls in the presence of nasal sample negative for MRSA. The efficiency of amplification and detection of the ICSPAD IC template inside *B. globigii* spores versus that of the purified ICAD IC template using the MRSA-specific assay is compared. All assays were performed in the presence of a nasal sample negative for MRSA which was collected from a volunteer. Panels A and C: Four repeats of amplification and detection of 100 copies per reaction of purified and linearized recombinant plasmid (i.e. ICAD controls) in the presence of a prepared MRSA-negative nasal sample (sample # AH-2 for Panel A; sample # MRB-2 for Panel C). The fluorescence signal is from the TET-labeled IC-specific probe. Panels B and D: same as Panels A and C except that the amplification and detection of the IC was from 500 spores per reaction of *B. globigii* carrying the IC template spiked into the tested nasal specimen prior to its preparation for PCR (i.e. ICSPAD controls).

In order to evaluate the use of *B. globigii* spores to provide an ICSPAD control, we have compared the amplication/detection efficiency of DNA extracted from *B. globigii* spores using the rapid DNA extraction procedure described in PCT patent publication WO 03/008636 (i.e. ICSPAD control) with that of the IC template present on the purified and linearized recombinant plasmid (i.e. ICAD control). Comparison of the performance of the cellular versus purified IC nucleic acid templates in the presence of nasal samples negative for MRSA showed that the performance and reproducibility of ICSPAD and ICAD controls was similar (FIG. 4). On average, around 500 spores of *B. globigii* per PCR reaction was found to be optimal as it did not interfere with MRSA detection and yielded reproducible IC template amplifications.

Figure 5:
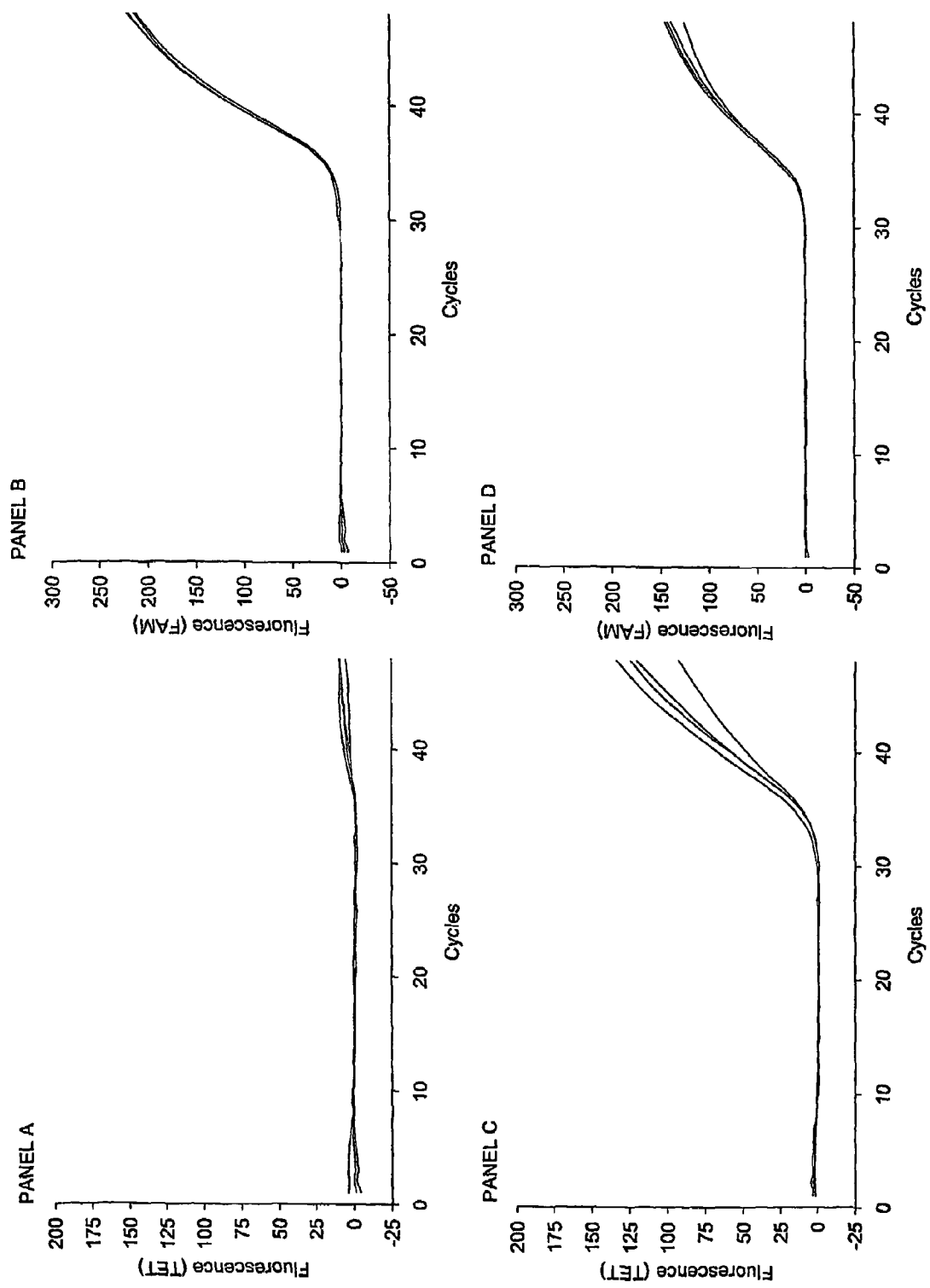
FIG. 5 shows ICSPAD versus ICAD controls in the presence of nasal sample spiked with MRSA cells. The efficiency of amplification and detection of the ICSPAD IC template inside *B. globigii* spores versus that of the purified ICAD IC template using the MRSA-specific assay is compared. All assays were performed in the presence of a nasal sample negative for MRSA and spiked with MRSA cells. These nasal samples were collected from volunteers. Panels A and E: Four repeats of amplification and detection of 100 copies per reaction of purified and linearized recombinant plasmid carrying the IC template (i.e. ICAD controls) in the presence of a prepared nasal sample (sample # AH-2 spiked with $1\times10^3$ MRSA cells from strain *S. aureus* ATCC 33592 for Panel A; sample # MRB-2 spiked with $1\times10^4$ MRSA cells of *S. aureus* ATCC 33592 for Panel E). The fluorescence signal is from the TET-labeled IC-specific probe. Panels B and F: Same as Panels A and E except that the fluorescence signal was from the FAM-labeled MRSA-specific probe. Panels C and G: same as Panels A and E except that the amplification and detection of the IC was from 500 spores per reaction of *B. globigii* carrying the IC template spiked into the tested nasal specimen prior to its preparation for PCR (i.e. ICSPAD controls). Panels D and H: Same as Panels C and G except that the fluorescence signal was from the FAM-labeled MRSA-specific probe.
Figure 5:
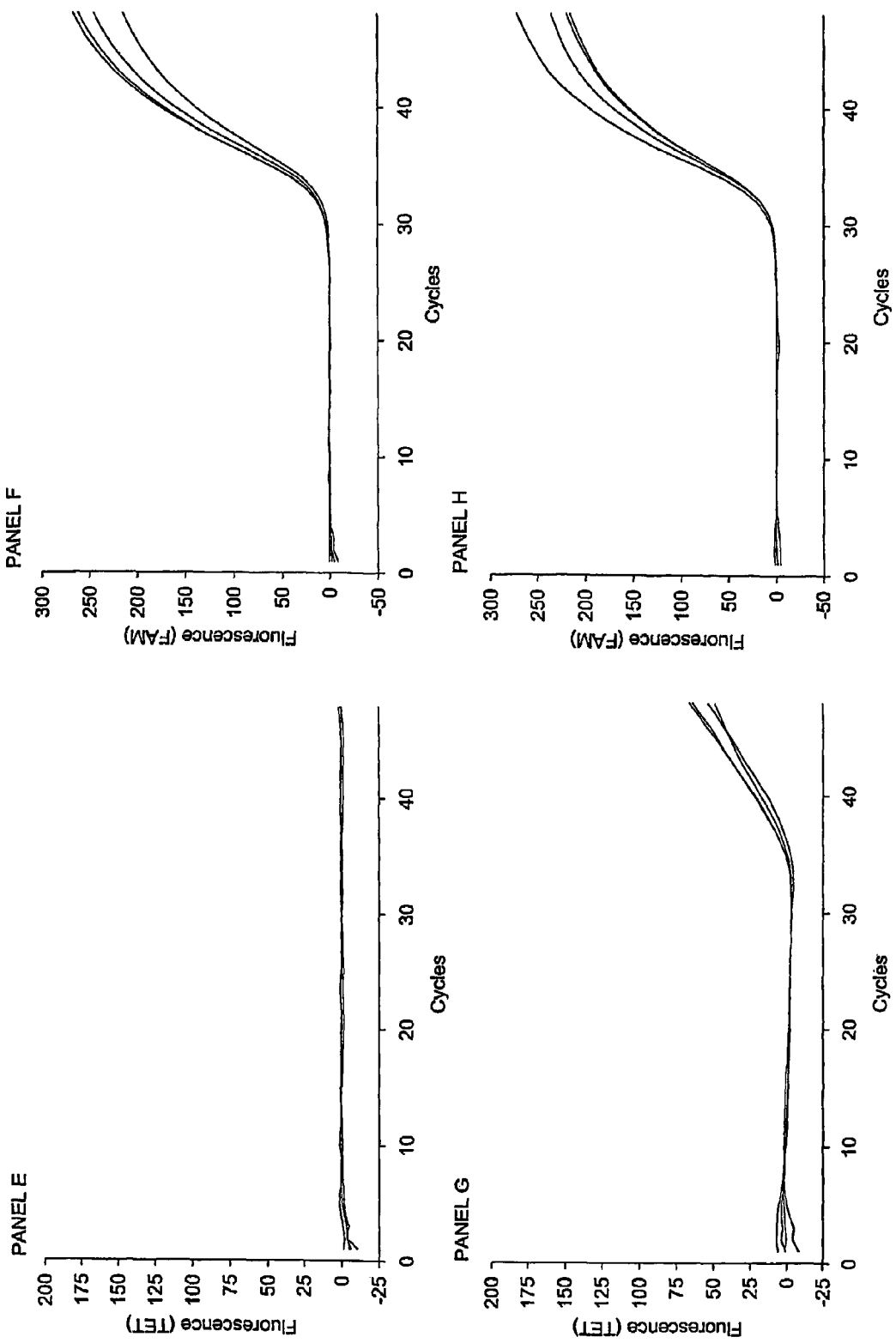

Testing with nasal samples spiked with *S. aureus* cells in mid-log growth phase, showed that the efficiency and reproducibility of the MRSA-specific amplification was similar with both ICSPAD and ICAD (FIG. 5). As expected, the signal from both types of IC was lower (i.e. higher cycle threshold values and/or lower fluorescence end points) in the presence of $1\times10^3$ and/or $1\times10^4$ *S. aureus* cells per PCR reaction. This phenomenon is explained by the competition for PCR reagents in the presence of a relatively important load of *S. aureus* cells. Under those circumstances, the requirement for a signal from the ICSPAD or ICAD control is not necessary since the test sample is clearly positive for the target analyte. In fact, ICSPAD or ICAD controls are particularly important to prevent false-negative results with samples negative for the target analyte(s) or with samples interfering with sample preparation, amplification and/or detection (e.g. incomplete cell lysis, PCR inhibition).

In conclusion, ICSPAD controls provided by using *B. globigii* spores added to the test sample prior to its preparation for PCR are as efficient and as reproducible as the commonly used ICAD controls using highly purified IC nucleic acid templates incorporated directly into the amplification/detection reaction mixture. The advantages of targeting IC templates within bacterial cells (i.e. ICSPAD control) as compared to the use of highly purified IC nucleic acid templates incorporated directly into the amplification/detection reaction mixture (i.e. ICAD control) are discussed in Example 1. Furthermore, the use of IC templates inside bacterial endospores (e.g. *B. globigii* spores), as described in the present example, confers the added advantage of providing a universal control for microbial cell lysis since bacterial spores are among the most difficult cells to lyse.

EXAMPLE 4

Monitoring of PCR Inhibition Using Cellular ICSPAD

Figure 6:
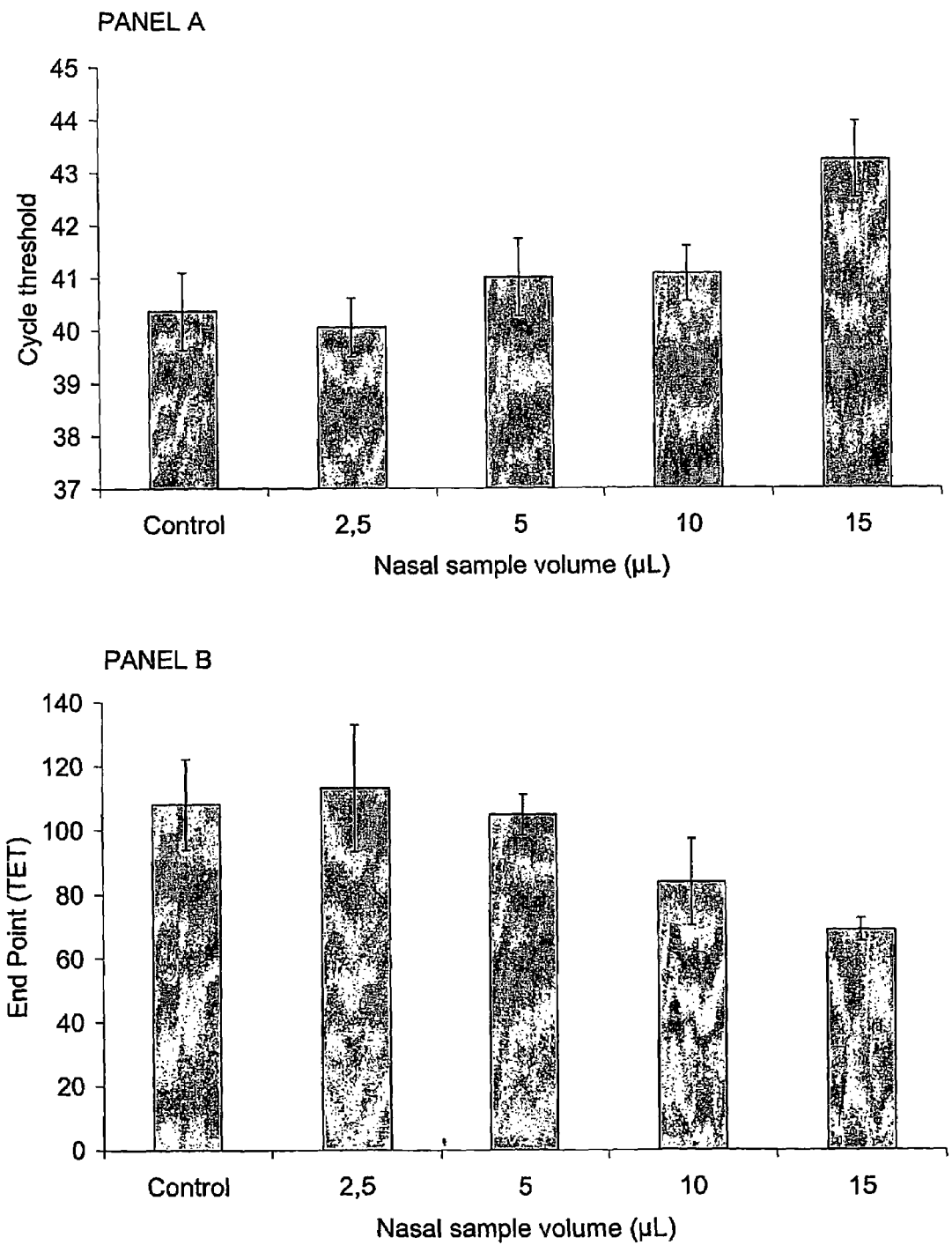
FIG. 6 shows a monitoring of PCR inhibition using ICSPAD controls. PCR amplifications were performed in the presence of 2.5, 5.0, 10, or 15 μL of a MRSA-negative nasal specimen (# AH-3) spiked with 500 *B. globigii* spores per reaction as compared to a control reaction. Three repeats were performed for each sample volume tested. Panel A: Cycle thresholds obtained with the different nasal sample volumes tested. Panel B: Fluorescence end points obtained with the different nasal sample volumes tested. The fluorescence signal is from the TET-labeled IC-specific probe. Standard deviations are shown for both panels.

Same as Example 3 except that various volumes of nasal specimen were tested using PCR reaction mixtures containing only the cellular IC and *B. globigii*-specific primers and probe. Nucleic acid amplifications were performed in the presence of 2.5, 5.0, 10, or 15 µL of nasal specimen spiked with approximately 500 spores per reaction (FIG. 6). These results show that the cellular ICSPAD allowed to monitor partial PCR inhibition associated with the presence of more than 2.5 µL of nasal specimen. Indeed, the performance of the assay was gradually reduced as the specimen volume increased (i.e. augmenting cycle threshold values and decreasing fluorescence end points).

EXAMPLE 5

Use of an IC Template Integrated into a *Bacillus* Strain

Same as Example 3 except that the IC template is integrated into the genome of a strain of *Bacillus*. The IC template may be incorporated into *Bacillus* cells using various molecular biology strategies including transformation, electroporation, conjugation or transduction of recombinant plasmids, transposons or bacteriophages carrying the IC template. The recombinant vector may be integrated into the *Bacillus* chromosome or into a plasmid via homologous recombination, or alternatively, may be stably maintained into the *Bacillus* host strain. The genetically engineered strain is then cultivated under conditions favoring sporulation. The spores are subsequently purified and treated to eliminate vegetative cells as described in Example 2 and used to spike a test sample as described in Example 3 to provide an ICSPAD control. The efficiency of the PCR amplification of the IC template incorporated into the *Bacillus* spores depends on the lysis efficiency of the spores. The main advantage of this ICSPAD method is that it provides a universal microbial cell lysis control since spores are among the most difficult cells to lyse.

EXAMPLE 6

Lysis Efficiency of *B. globigii* Spores

The *B. globigii* spores prepared as described in Example 2 were tested with the protocol of PCT patent publication WO 03/008636 for rapid DNA extraction from microbial cells. PCR amplification was performed as described in Example 3. The IC-specific amplification/detection was monitored in real-time by measuring the fluorescence signal at every PCR cycle.

Figure 7:
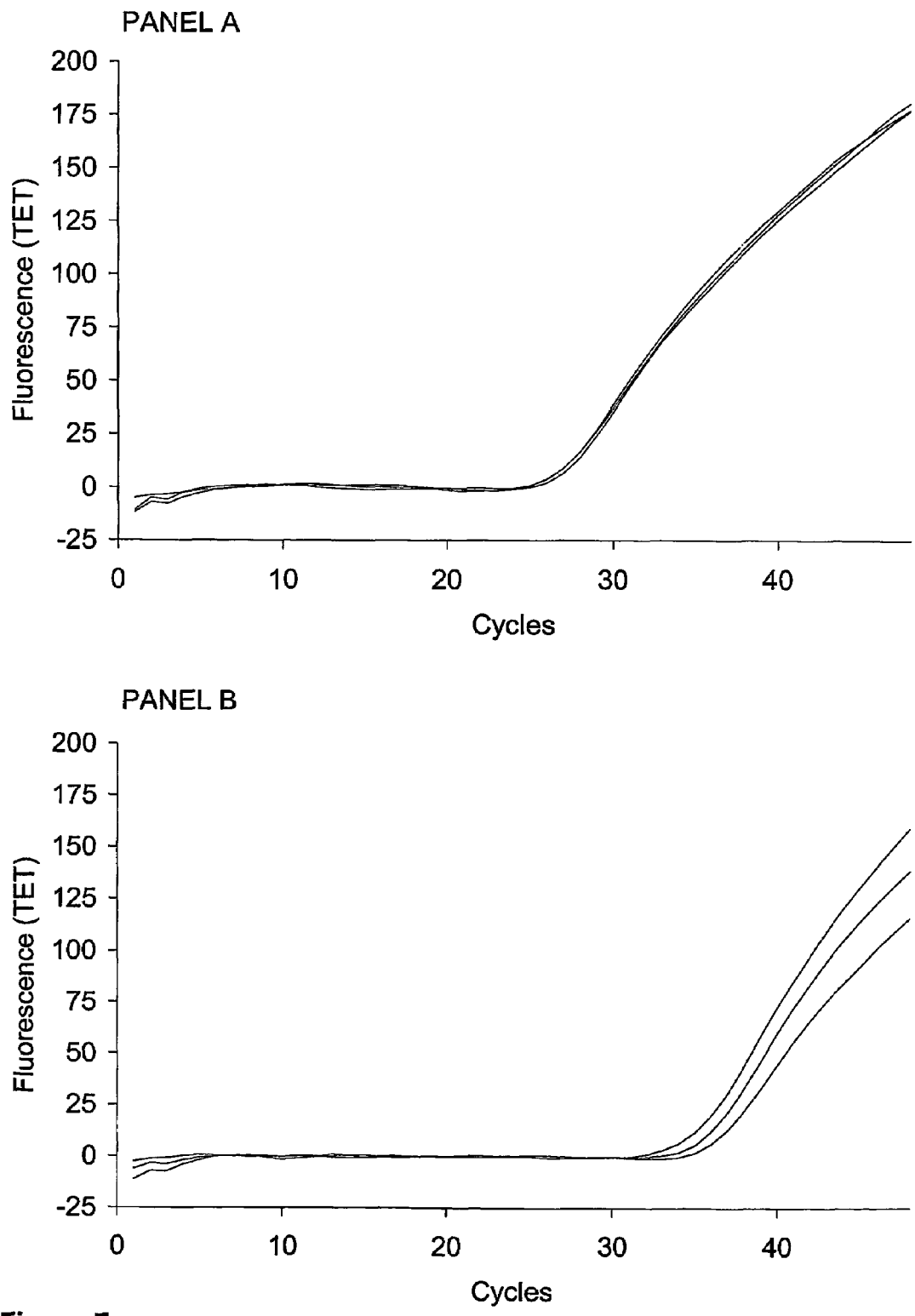
FIG. 7 shows lysis efficiency of *B. globigii* spores. The efficiency of amplification and detection of DNA extracted from treated spores versus that of DNA extracted from untreated spores using the MRSA-specific PCR assay is compared. Panel A: Three repeats of amplification and detection of DNA extracted from treated spores. Panel B: Three repeats of amplification and detection of DNA extracted from untreated spores. The fluorescence signal is from the TET-labeled IC-specific probe for both panels.

The efficiency of DNA recovery from *B. globigii* spores using the rapid DNA extraction method was compared with DNA recovery from untreated spores (FIG. 7). These results show a difference of about 8 cycle thresholds which suggest a spore lysis efficiency of at least 99%. Furthermore, PCR amplification of DNA from the treated spores was more reproducible than PCR from untreated spores (FIG. 7). These results also demonstrate the importance of using cellular IC spiked into a test sample to verify the efficiency of cell lysis. This is particularly important for hard-to-lyse cells such as bacterial spores. Therefore, bacterial spores represent a system of choice to monitor the efficiency of a universal cell lysis method.

EXAMPLE 7

Same as Example 1, 3 or 5 except that the IC nucleic acid template is into a cell other than a *Bacillus* spore or an *E. coli* vegetative cell.

EXAMPLE 8

Same as Example 1, 3 or 5 except that the IC nucleic acid template is into a viral particle.

EXAMPLE 9

Same as Example 1, 3 or 5 except that the IC nucleic acid template is into an organelle.

EXAMPLE 10

Same as Example 1, 3 or 5 except that the IC nucleic acid template is into a cell comprising an organelle and/or a viral particle.

Although the present invention has been described hereinabove by way of embodiments thereof, it can be modified, without departing from the spirit, scope and nature of the subject invention as defined in the appended claims.

What is claimed is:

1. A method for verifying the efficiency of sample preparation of test sample nucleic acids and the performance of nucleic acid amplification and detection practiced on a test sample after its preparation, said method comprising:
   (i) providing a universal internal control reagent comprising a bacterial spore, said internal control reagent having at least one internal control (IC) nucleic acid target sequence therein, wherein said internal control reagent is an internal control for the release, amplification, and detection of a nucleic acid from said test sample;
   (ii) mixing said internal control reagent and said test sample;
   (iii) submitting said test sample mixed with said internal control reagent to a sample preparation procedure in order to release both said nucleic acid from said test sample and said IC nucleic acid target sequence from said internal control reagent; and
   (iv) submitting a product from said sample preparation procedure to amplification and detection for the amplification and detection of both said IC nucleic acid target sequence and said nucleic acid of the test sample, wherein detection of said IC nucleic acid target sequence is indicative of both efficient sample preparation and performance of nucleic acid amplification.

2. The method as defined in claim 1, further comprising
   (v) comparing the amplification and detection performed in (iv) to the amplification and detection performed with a control reaction to evaluate the efficiency of the sample preparation and the performance of the nucleic acid amplification and detection practiced on said test sample and reagent.

3. The method of claim 1, wherein said sample preparation procedure comprises concentrating and/or purifying cells, spores, or cells comprising organelles and/or viral particles prior to lysis.

4. The method of claim 1, wherein said spore is a *Bacillus* spore.

5. The method of claim 4, wherein said spore is a *Bacillus globigii* spore.

6. The method of claim 1, wherein said IC nucleic acid target sequence is on a cloning vector.

7. The method of claim 1, wherein said IC nucleic acid target sequence is on a plasmid vector.

8. The method of claim 1, wherein said nucleic acid amplification method is PCR.

9. The method of claim 1, wherein said IC nucleic acid target sequence is nucleic acid sequence of clinical, environmental, alimentary or human origin.

10. The method of claim 1, wherein said IC nucleic acid target sequence is a nucleic acid sequence of microbial origin.

11. The method of claim 1, wherein the said test sample is a sample of clinical, environmental or alimentary origin.

12. The method of claim 1, wherein said test sample comprises a vaginal/anal or a nasal swab.

13. The method of claim 1, wherein said sample preparation procedure comprises
   (i) concentration and/or purification of cells, spores or cells comprising organelles and/or viral particles,
   (ii) lysis of cells, spores, or cells comprising organelles and/or viral particles,
   (iii) nucleic acid extraction,
   (iv) elimination, neutralization and/or inactivation of nucleic acid testing (NAT) inhibitors, and/or
   (v) nucleic acid concentration and/or purification.

14. A method for verifying the efficiency of sample preparation of test sample nucleic acids and the performance of nucleic acid amplification and detection practiced on a test sample after its preparation, said method comprising:
   (i) providing a universal internal control reagent comprising a bacterial spore, said internal control reagent having at least one internal control (IC) nucleic acid target sequence therein, wherein said internal control reagent is an internal control for the release, amplification and detection of a nucleic acid from said test sample;
   (ii) mixing said internal control reagent and said test sample;
   (iii) submitting said test sample with said mixed internal control reagent to a nucleic acid amplification procedure in order to release both said nucleic acid from said test sample and said IC nucleic acid target sequence from said internal control reagent; and
   (iv) submitting a product from said amplification procedure to further amplification or detection for the amplification or detection of both said IC nucleic acid target sequence and said nucleic acid of the test sample, wherein detection of said IC nucleic acid target sequence is indicative of both efficient sample preparation and performance of nucleic acid amplification.

15. The method of claim 14, wherein said sample preparation procedure comprises concentrating and/or purifying cells, spores, or cells comprising organelles and/or viral particles prior to lysis.

16. The method of claim 14, wherein said spore is a *Bacillus* spore.

17. The method of claim 16, wherein said spore is a *Bacillus globigii* spore.

18. The method of claim 14, wherein said IC nucleic acid target sequence is on a cloning vector.

19. The method of claim 14, wherein said IC nucleic acid target sequence is on a plasmid vector.

20. The method of claim 14, wherein said nucleic acid amplification method is PCR.

21. The method of claim 14, wherein said IC nucleic acid target sequence is nucleic acid sequence of clinical, environmental, alimentary or human origin.

22. The method of claim 14, wherein said IC nucleic acid target sequence is a nucleic acid sequence of microbial origin.

23. The method of claim 14 wherein the said test sample is a sample of clinical, environmental or alimentary origin.

24. The method of claim 14, wherein said test sample comprises a vaginal/anal or a nasal swab.

25. The method of claim 14, wherein said sample preparation method comprises
   (i) concentration and/or purification of cells, spores, or cells comprising organelles and/or viral particles,
   (ii) lysis of cells, organelles or cells comprising organelles and/or viral particles,
   (iii) nucleic acid extraction,
   (iv) elimination, neutralization and/or inactivation of nucleic acid testing (NAT) inhibitors, and/or
   (v) nucleic acid concentration and/or purification.

26. The method of claim 1, wherein said amplification reaction comprises contacting said product from said sample preparation procedure with a primer pair comprising SEQ ID NO:7 and SEQ ID NO:8.

27. The method of claim 14, wherein said amplification reaction comprises contacting said product from said sample preparation procedure with a primer pair comprising SEQ ID NO:7 and SEQ ID NO:8.

28. The method of claim 1, wherein said spore is purified prior to mixing with said test sample.

29. The method of claim 14, wherein said spore is purified prior to mixing with said test sample.

30. The method of claim 28, wherein said purification eliminates vegetative cells from said internal control reagent.

31. The method of claim 19, wherein said purification eliminates vegetative cells from said internal control reagent.

32. The method of claim 1, wherein said internal control reagent comprises about 500 spores.

33. The method of claim 14, wherein said internal control reagent comprises about 500 spores.

34. The method of claim 1, wherein said amplification reaction comprises contacting said product from said sample preparation procedure with a first primer pair designed to amplify said internal control nucleic acid target, and a second primer pair designed to amplify said nucleic acid from said test sample, wherein the first and second primer pairs are different.

35. The method of claim 14, wherein said amplification reaction comprises contacting said product from said sample preparation procedure with a first primer pair designed to amplify said internal control nucleic acid target, and a second primer pair designed to amplify said nucleic acid from said test sample, wherein the first and second primer pairs are different.

36. The method of claim 34, wherein the amplification product of said second primer pair is shorter than the amplification product of said first primer pair.

37. The method of claim 35, wherein the amplification product of said second primer pair is shorter than the amplification product of said first primer pair.

* * * * *